(12) United States Patent
Siejko et al.

(10) Patent No.: US 9,451,893 B2
(45) Date of Patent: Sep. 27, 2016

(54) CALCULATION OF SELF-CORRELATION IN AN IMPLANTABLE CARDIAC DEVICE

(71) Applicant: CAMERON HEALTH, INC., St. Paul, MN (US)

(72) Inventors: Krzysztof Z. Siejko, Maple Grove, MN (US); Paul Huelskamp, St. Paul, MN (US)

(73) Assignee: CAMERON HEALTH, INC., St. Paul, MN (US)

(*) Notice: Subject to any disclaimer, the term of this patent is extended or adjusted under 35 U.S.C. 154(b) by 0 days.

(21) Appl. No.: 14/819,889

(22) Filed: Aug. 6, 2015

(65) Prior Publication Data

US 2016/0045136 A1 Feb. 18, 2016

Related U.S. Application Data

(60) Provisional application No. 62/038,440, filed on Aug. 18, 2014, provisional application No. 62/038,437, filed on Aug. 18, 2014, provisional application No. 62/038,438, filed on Aug. 18, 2014.

(51) Int. Cl.
*A61B 5/0452* (2006.01)
*A61B 5/042* (2006.01)
*A61B 5/04* (2006.01)
(Continued)

(52) U.S. Cl.
CPC ......... *A61B 5/04012* (2013.01); *A61B 5/0422* (2013.01); *A61B 5/0456* (2013.01); *A61B 5/04525* (2013.01); *A61B 5/4836* (2013.01); *A61B 5/686* (2013.01); *A61N 1/3704* (2013.01); *A61N 1/3925* (2013.01); *A61N 1/3956* (2013.01); *A61N 1/3987* (2013.01); *G06F 17/16* (2013.01); *A61B 5/0245* (2013.01); *A61B 5/046* (2013.01); *A61B 5/04011* (2013.01); *A61B 5/04014* (2013.01); *A61B 5/0464* (2013.01); *A61B 5/7246* (2013.01)

(58) Field of Classification Search
None
See application file for complete search history.

(56) References Cited

U.S. PATENT DOCUMENTS 4,239,048 A 12/1980 Steuer
5,243,993 A 9/1993 Alexander et al.
(Continued)

FOREIGN PATENT DOCUMENTS

WO 2012135062 A1 10/2012
WO 2013160538 A1 10/2013

OTHER PUBLICATIONS

International Application No. PCT/2015/045158, "Invitation to Pay Additional Fees and, where Applicable, Protest Fee," Jan. 13, 2016.
(Continued)

*Primary Examiner* — Brian T Gedeon
(74) *Attorney, Agent, or Firm* — Seager, Tufte & Wickhem LLP

(57) ABSTRACT

Self-correlation enhancements and implementations are described. In particular, certain examples demonstrate the analytical tools to reduce the computational burden of generating a self-correlation function within an implantable medical device. Peak selector and tracking analysis are also included as secondary elements for identifying and generating confidence in rate estimates based on the self-correlation function. The approach may enable an alternative calculation of cardiac rate in an implantable medical device as a stand-alone rate detector or as a double-check of other rate calculations.

20 Claims, 16 Drawing Sheets

(51) Int. Cl.
    *A61N 1/39*     (2006.01)
    *A61B 5/0456*     (2006.01)
    *A61B 5/00*     (2006.01)
    *G06F 17/16*     (2006.01)
    *A61N 1/37*     (2006.01)
    *A61B 5/0245*     (2006.01)
    *A61B 5/046*     (2006.01)
    *A61B 5/0464*     (2006.01)

(56) References Cited

U.S. PATENT DOCUMENTS

| | | |
|---|---|---|
| 5,558,096 A | 9/1996 | Palatnik |
| 5,709,215 A | 1/1998 | Perttu et al. |
| 5,857,977 A | 1/1999 | Caswell et al. |
| 6,567,691 B1 | 5/2003 | Stadler |
| 6,647,292 B1 | 11/2003 | Bardy et al. |
| 6,721,597 B1 | 4/2004 | Bardy et al. |
| 7,149,575 B2 | 12/2006 | Ostroff et al. |
| 7,194,302 B2 | 3/2007 | Bardy et al. |
| 7,248,921 B2 | 7/2007 | Palreddy et al. |
| 7,623,909 B2 | 11/2009 | Sanghera et al. |
| 8,160,686 B2 | 4/2012 | Allavatam et al. |
| 8,160,687 B2 | 4/2012 | Warren et al. |
| 8,200,341 B2 | 6/2012 | Sanghera et al. |
| 8,265,737 B2 | 9/2012 | Warren et al. |
| 8,409,107 B2 | 4/2013 | Sweeney et al. |
| 8,457,737 B2 | 6/2013 | Bardy et al. |
| 8,521,276 B2 | 8/2013 | Sweeney et al. |
| 8,565,878 B2 | 10/2013 | Allavatam et al. |
| 8,744,555 B2 | 6/2014 | Allatam et al. |
| 8,942,802 B2 | 1/2015 | Ostroff et al. |
| 2006/0004547 A1 | 1/2006 | Mostafavi |
| 2009/0315889 A1 | 12/2009 | Tognola |
| 2012/0197151 A1 | 8/2012 | Schatz et al. |
| 2012/0271367 A1 | 10/2012 | Qu et al. |
| 2013/0079657 A1 | 3/2013 | Ochs et al. |
| 2014/0073960 A1 | 3/2014 | Rodriguez-Llorente et al. |
| 2014/0180154 A1 | 6/2014 | Sierra et al. |

OTHER PUBLICATIONS

International Application No. PCT/US2015/045157, "Notification of Transmittal of the International Search Report and the Written Opinion of the International Searching Authority, or the Declaration," Oct. 19, 2015.

PCT Application No. US2015/045159, The International Search Report and the Written Opinion of the International Searching Authority. 14 Pages. Dated: Dec. 8, 2015.

CALCULATION OF SELF-CORRELATION IN AN IMPLANTABLE CARDIAC DEVICE

CROSS-REFERENCE TO RELATED PATENT DOCUMENTS

The present application claims the benefit of and priority to each of U.S. Provisional Patent Application No. 62/038,440, filed Aug. 18, 2014, and titled CALCULATION OF SELF-CORRELATION IN AN IMPLANTABLE CARDIAC DEVICE, U.S. Provisional Patent Application No. 62/038,437, filed Aug. 18, 2014, and titled CARDIAC RATE TRACKING IN AN IMPLANTABLE MEDICAL DEVICE, and U.S. Provisional Patent Application No. 62/038,438, filed Aug. 18, 2014, and titled PEAK SELECTION FOR SELF CORRELATION ANALYSIS OF CARDIAC RATE IN AN IMPLANTABLE MEDICAL DEVICE, the disclosures of which are incorporated herein by reference. The present application is also related to U.S. patent application Ser. No. 14/819,817, filed on even date herewith and titled CARDIAC RATE TRACKING IN AN IMPLANTABLE MEDICAL DEVICE, and U.S. patent application Ser. No. 14/819,851, filed on even date herewith, and titled PEAK SELECTION FOR SELF CORRELATION ANALYSIS OF CARDIAC RATE IN AN IMPLANTABLE MEDICAL DEVICE, the disclosures of which are incorporated herein by reference.

BACKGROUND

Implantable defibrillators are designed to deliver an electrical stimulus to terminate certain deleterious arrhythmias. Such devices must accurately identify dangerous arrhythmias (sensitivity). They must also avoid delivering electrical stimulus when not desired (specificity). Attaining high sensitivity and specificity in the discrimination of such deleterious arrhythmias is a challenge.

Typically treatable arrhythmias include ventricular fibrillation (VF) and/or polymorphic ventricular tachycarrhythmia (PVT). Other arrhythmias can include monomorphic ventricular tachyarrhythmia (MVT), atrial fibrillation (AF), and atrial flutter (Flutter), with the atrial arrhythmias of AF and Flutter deemed supraventricular tachyarrhythmias (SVT). For some patients, MVT is treated by the implantable defibrillator using anti-tachycardia pacing (ATP), while AF and Flutter are typically addressed by other therapies entirely. In addition, patients can experience exercise induced ventricular tachycardia (VT), which is typically not treated at all. Some patients experience bundle branch blocks and other conditions that can arise at elevated rates, causing the signal shape (morphology) of the cardiac signal with each cardiac beat to change relative to morphology at slower rates. Implantable devices are expected to appropriately distinguish these various conditions and apply the correct therapy for only certain conditions.

Chen et al., in Ventricular Fibrillation Detection By A Regression Test On The Autocorrelation Function, *Med Biol Eng Comput*; 25 (3): 241-9 (May, 1987), discuss the use of an autocorrelation function (ACF) to identify ventricular fibrillation in which the ACF is performed. Chen et al. hypothesize that the peaks in the ACF output are expected to be periodic and/or regular and should pass a linear regression test when a ventricular tachycardia (VT) is occurring. Therefore, the results of the ACF are subjected to a linear regression analysis and VF is declared if the linear regression fails to find a linear fit. Chen et al. limit their analysis to VF and VT and do not address the fact that the linear regression they discuss would also likely fail for supraventricular arrhythmias such as atrial flutter or atrial fibrillation for which defibrillation therapy is typically not desired. Moreover, adding a linear regression test with ACF would create a very large computational burden for an implantable system.

Sweeney et al., in U.S. Pat. Nos. 8,409,107 and/or 8,521,276 discuss the use of an ACF applied to a transformation of detected cardiac signal using curve matching. The ACF would be applied to identify recurring curves. Such recurring curves could be used to find heart beats from the transformed signal, which could be used to calculate rate. ACF is not directly applied to the time varying cardiac signal, however.

ACF in each of these examples involves a large number of computational steps to be calculated. To make ACF more useful in an implantable device, simplified methods and alternative methods which address the spectrum of potential arrhythmias are desired.

OVERVIEW

The present inventors have recognized, among other things, that a problem to be solved can include the incorporation of a modified autocorrelation function into an implantable cardiac device. Modifications can be made to reduce the computational burden of the correlation function and accommodate some of the difficulties which arise in the context of an implantable device monitoring cardiac function. The present subject matter can help provide a solution to the problem of enhancing sensitivity and specificity in implantable cardiac rhythm management devices.

The present invention comprises several separately implementable elements which provide avenues for reliable use of ACF at lesser computational burden in an implantable device.

In a first aspect, the invention comprises a set of rules for the calculation of a Minimum Absolute Difference (MAD) function to construct a Self Correlation. The use of MAD facilitates a far simpler and less computationally intensive manner of analyzing the cardiac signal than ACF.

In a second aspect, the invention comprises a set of rules for the identification and selection of candidate peaks within a Self Correlation or ACF to yield an estimate of heart rate.

In a third aspect, the present invention comprises a set of rules for tracking cardiac rate over time using output peaks from either a Self Correlation or ACF.

The first, second and third aspects may each be used independent of the other aspects, or in any suitable combination such as first-second, first-third, or second-third.

In a fourth aspect, the present invention comprises an integrated system or method in which a simplified Self Correlation of the first aspect is combined with the second and third aspects.

In various embodiments, devices and methods may use any of the first through fourth aspects either on a continuing basis or following a triggering event. The present disclosure is, in certain examples, directed to enhancements such that a self-correlation function can take the form of a simplified ACF, such as an MAD, as further discussed below. Enhancements which that aid in selecting peaks within the results of a self-correlation function are discussed still further in U.S. Provisional Patent Application No. 62/038,438, filed Aug. 18, 2014, and titled PEAK SELECTION FOR SELF CORRELATION ANALYSIS OF CARDIAC RATE IN AN IMPLANTABLE MEDICAL DEVICE, the disclosure of which is incorporated herein by reference. Tracking analysis, such as that in U.S. Provisional Patent Application No. 62/038,437, filed Aug. 18, 2014, and titled CARDIAC RATE TRACKING IN AN IMPLANTABLE MEDICAL DEVICE, uses the results of peak selection to provide a rate estimate for use in therapy and other decisions over time, with added confidence based on repeated peak selection. Some examples of the present invention may omit or use alternatives to these peak selection and tracking enhancements.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
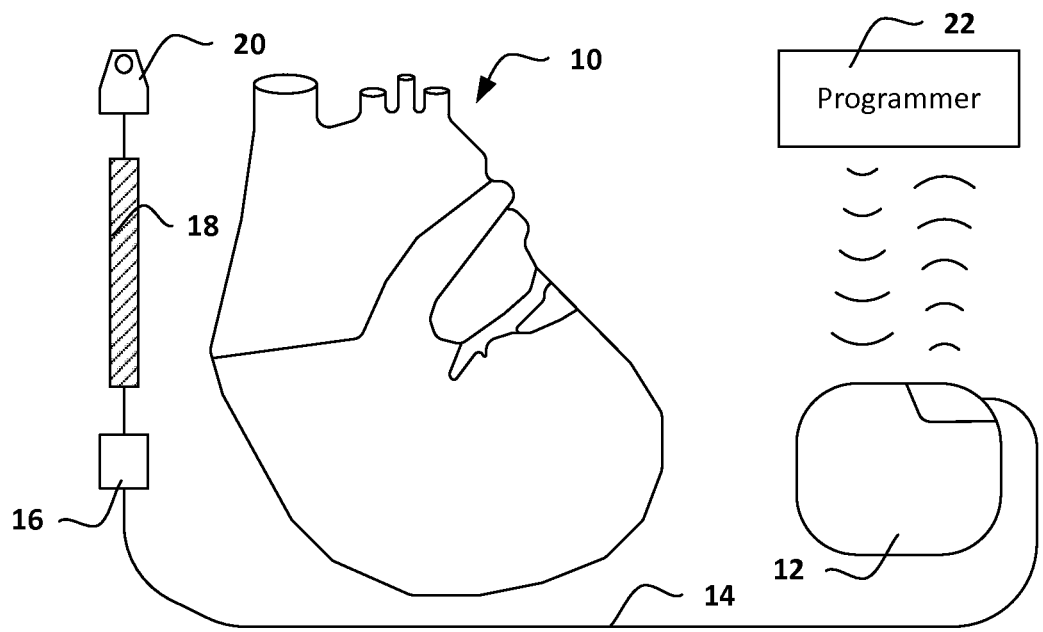
FIG. 1 shows a subcutaneously implanted cardiac treatment system.
Figure 2:
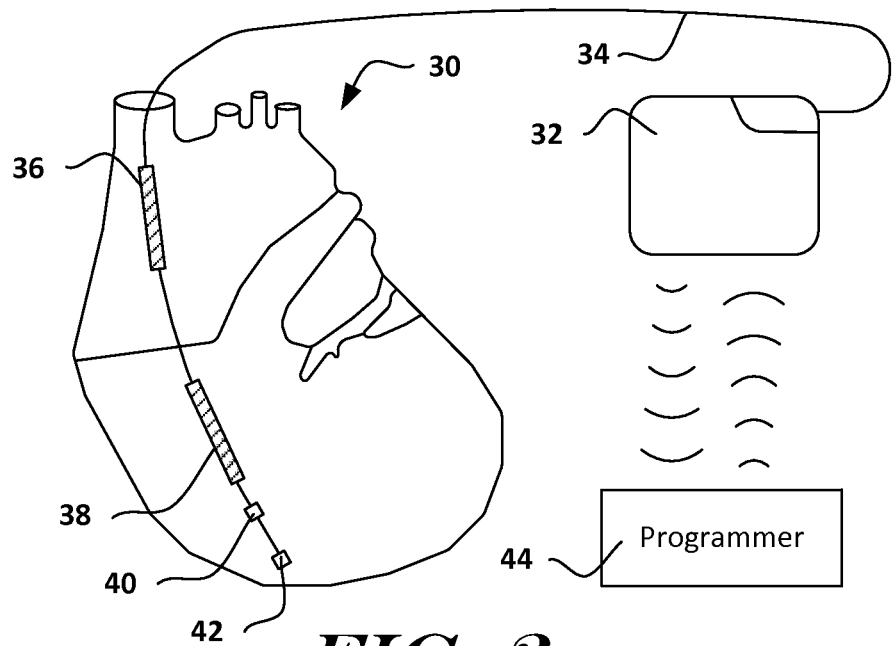
FIG. 2 shows a transvenously implanted cardiac treatment system.

FIGS. 1-2 show implant locations for illustrative cardiac systems. The present invention may find application in a subcutaneous-only system as illustrated in FIG. 1, or in a transvenous system as shown in FIG. 2. Alternatives may include systems having multiple subcutaneous, transvenous and/or intracardiac elements, epicardial systems, or fully intravenous or intracardiac systems.

The illustrative system shown in FIG. 1 is shown relative to a heart 10 and is intended to convey a subcutaneous implant that would take place over the ribs of the patient and beneath the patient's skin. A canister 12 is implanted near the left axilla, with lateral, anterior, or posterior positions being possible. A lead 14 couples the canister 12 to electrodes 16, 18 and 20, which are illustrated as implanted along the sternum of the patient, typically to the left or right thereof. The system in FIG. 1 may include an external programmer 22 configured for communication with the implant 12.

The system in FIG. 2 is a transvenous system, illustratively shown relative to the heart 30 again with the patient's ribs omitted for clarity. The canister 32 is in a high pectoral position, with the lead 34 accessing the vasculature and entering the heart. The lead 34 may include a superior vena cava coil electrode 36, a right ventricular coil electrode 38, and one or two ventricular sense/pace electrodes 40, 42. Again a programmer is shown at 44 and configured for communication with the implanted system. The system may further include a left ventricular lead (not shown).

Communication for either of the systems in FIG. 1 or 2 may be inductive, RF, direct (that is, using the patient's own tissue as a communication medium), or via any other suitable medium of communication. Such communication can be useful to configure the implanted system for sensing, therapy or other feature, to load new software or firmware for the implanted system, and to retrieve information about system operation such as device status, therapy history, diagnostic data (both device and patient related), or other suitable data. The programmers may contain such circuitry as is needed to provide processing, memory, display, telemetry/RF communications and the like for these noted purposes.

The canisters in FIGS. 1 and 2 will typically contain operational circuitry for the implantable system. The operational circuitry may include a controller and any suitable analog and/or digital circuits needed for signal processing, memory storage and generation of high-power electrical, low-power electrical and/or non-electrical outputs. For example, an analog to digital converter (ADC) can be a direct conversion ADC, a successive approximation ADC, a ramp comparing ADC, a Wilkinson ADC, an integrating, dual slope or multi-slope ADC, a pipeline ADC, or a sigma-delta ADC. Other ADC types, a modifications and/or hybrids of any of these types, may instead be used as those skilled in the art will appreciate.

The operational circuitry may be coupled to suitable battery technology for an implantable device, with any of numerous examples well known in the art, and may use various capacitor technologies to assist in the short term build-up and/or storage of energy for defibrillation or other high output purposes. For example, therapy delivery circuitry may include a combination of a transformer, diodes, and high power capacitors may be used to develop high voltages for storage on the capacitors, with switching circuitry for controlling delivery of the high voltages to the patient, for example, a flyback transformer circuit may be used with high power capacitors and an H-bridge circuit, as is known to the skilled artisan. The leads and external shell for the canisters can be manufactured with various materials suitable for implantation, such as those widely known, along with coatings for such materials, throughout the art. For example, the canisters can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes can be formed of suitable materials as well, such as silver, gold, titanium or stainless steel such as MP35N stainless steel alloy, or other materials.

The location of system implant may vary. For example, the system shown in FIG. 1 is a subcutaneous-only system located on the anterior and lateral chest between the skin and ribcage of the patient. Other subcutaneous only systems (including systems without a lead 14, with multiple leads 14, or an array in place of lead 14) may be used with other anterior only placements and/or anterior-posterior, posterior only, left-right, etc. locations, including, for example, locations noted in U.S. Pat. Nos. 6,647,292, 6,721,597, 7,149,575, 7,194,302, each of which is incorporated herein by reference, and other locations as well. Subcutaneous placement can include any location between the skin and ribcage, including sub-muscular.

Illustrative transvenous systems, in addition to that of FIG. 2, include single chamber, dual chamber and biventricular systems. A fully intravenous system has also been proposed. Additional or other coatings or materials than those noted above may be used, particularly for epicardial, transvenous or intravenous systems, leads and canisters. Systems may further include an implantable "seed" that can attach directly to the myocardium without a lead at all. Some systems may combine an implantable, intracardiac seed with a subcutaneous-only defibrillator, with the seed and defibrillator enabled for two-way communication such as commanded therapy delivery and/or conveyance of sensed data.

Various alternatives and details for these designs, materials and implantation approaches are known to those skilled in the art. Commercially available systems in which the above methods can be performed or which may be configured to perform such methods are known including the Boston Scientific Teligen™ ICD and S-ICD™ System, Medtronic Concerto™ and Virtuoso™ systems, and St. Jude Medical Promote™ RF and Current™ RF systems. Such platforms include numerous examples and alternatives for the various system elements.

As shown and described there are various ways in which an implantable cardiac rhythm management device or system may be implemented with respect to the current invention. In several examples, the methods and devices that are focused upon in the present invention include the ability to capture and analyze a far-field cardiac signal. Some examples of far-field signals include a signal captured between two subcutaneously placed electrodes, or between a canister electrode and an intracardiac electrode. Near field signals and/or signals generated as a combination of near and far field signals may be assessed in other alternatives.

Figure 3:
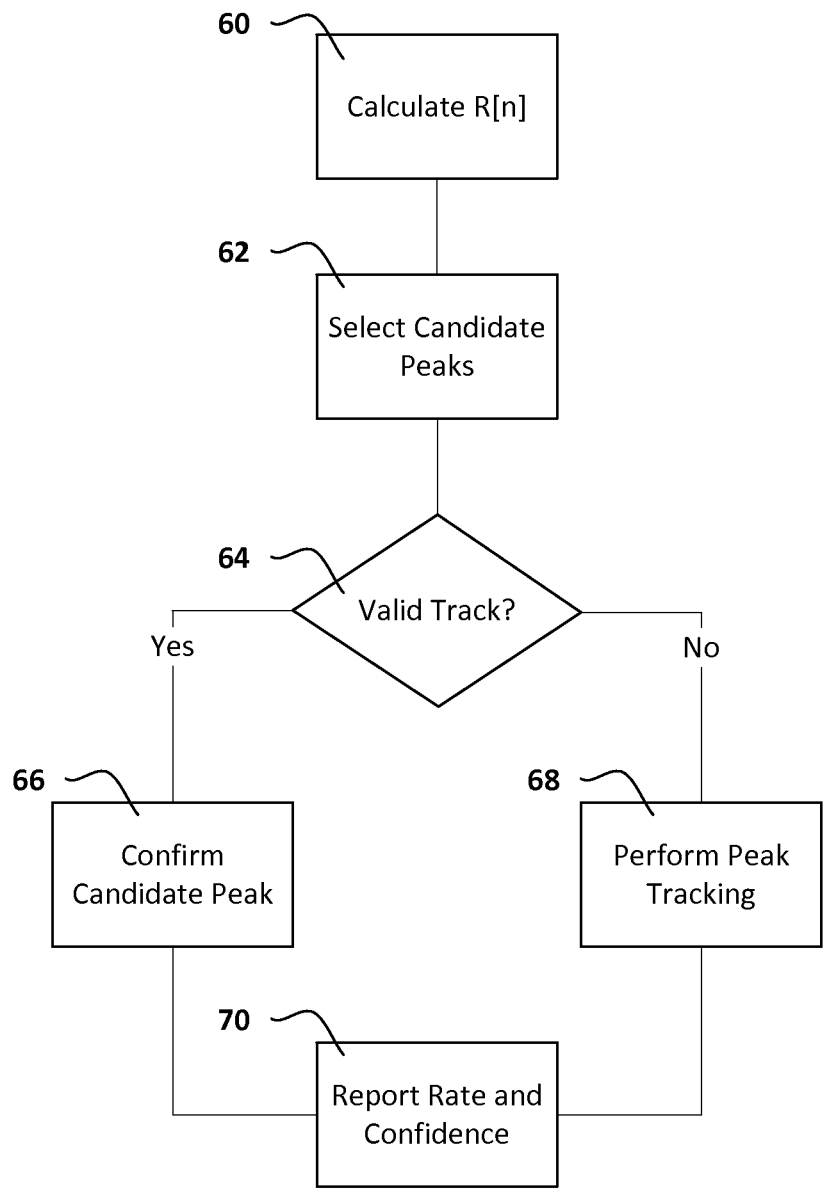
FIG. 3 shows an overall method for generating a cardiac rate estimate.
Figure 4:
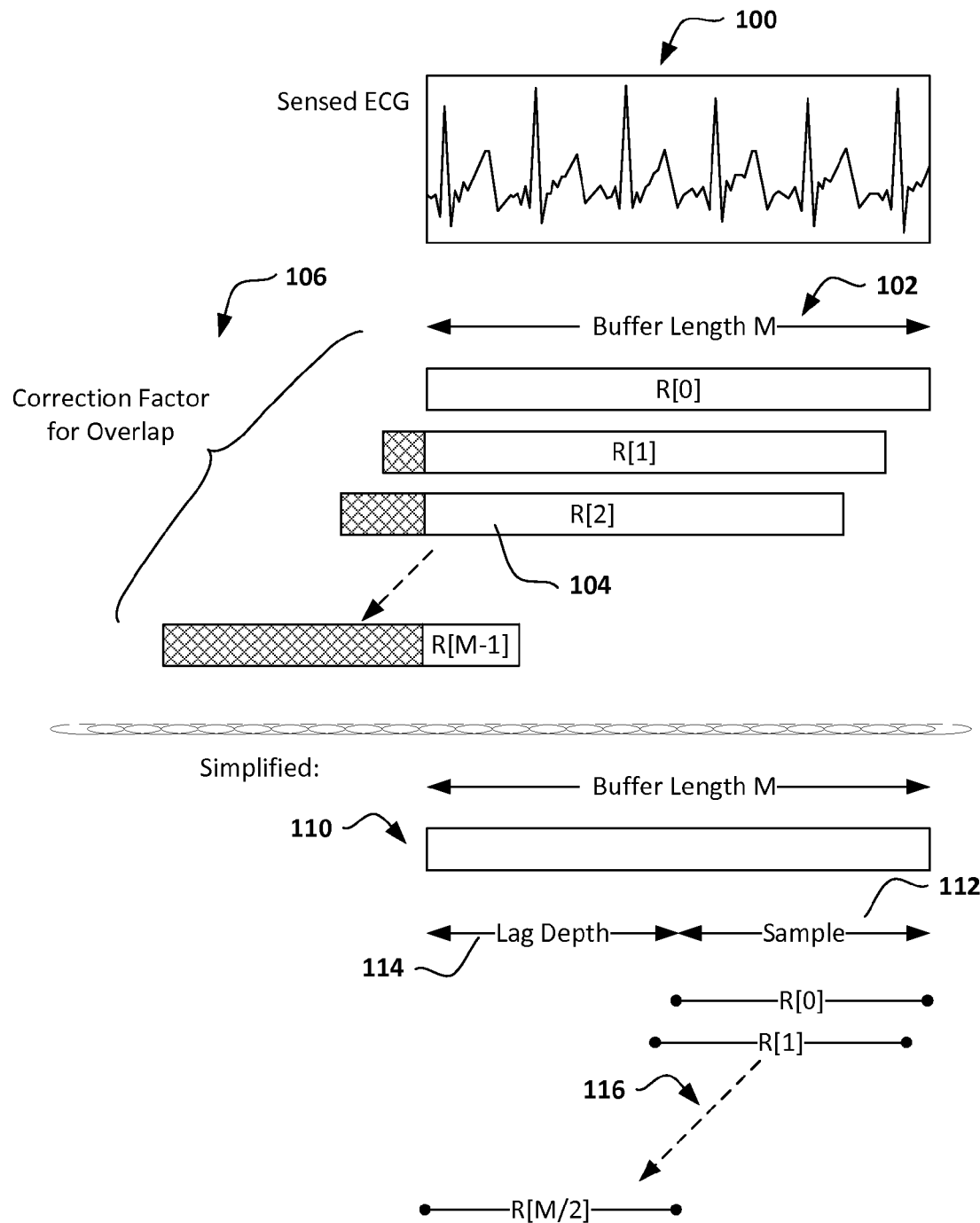
FIGS. 4-5 illustrate the analysis of data using a self-correlation function and differentiate such analysis from ACF.
Figure 5:
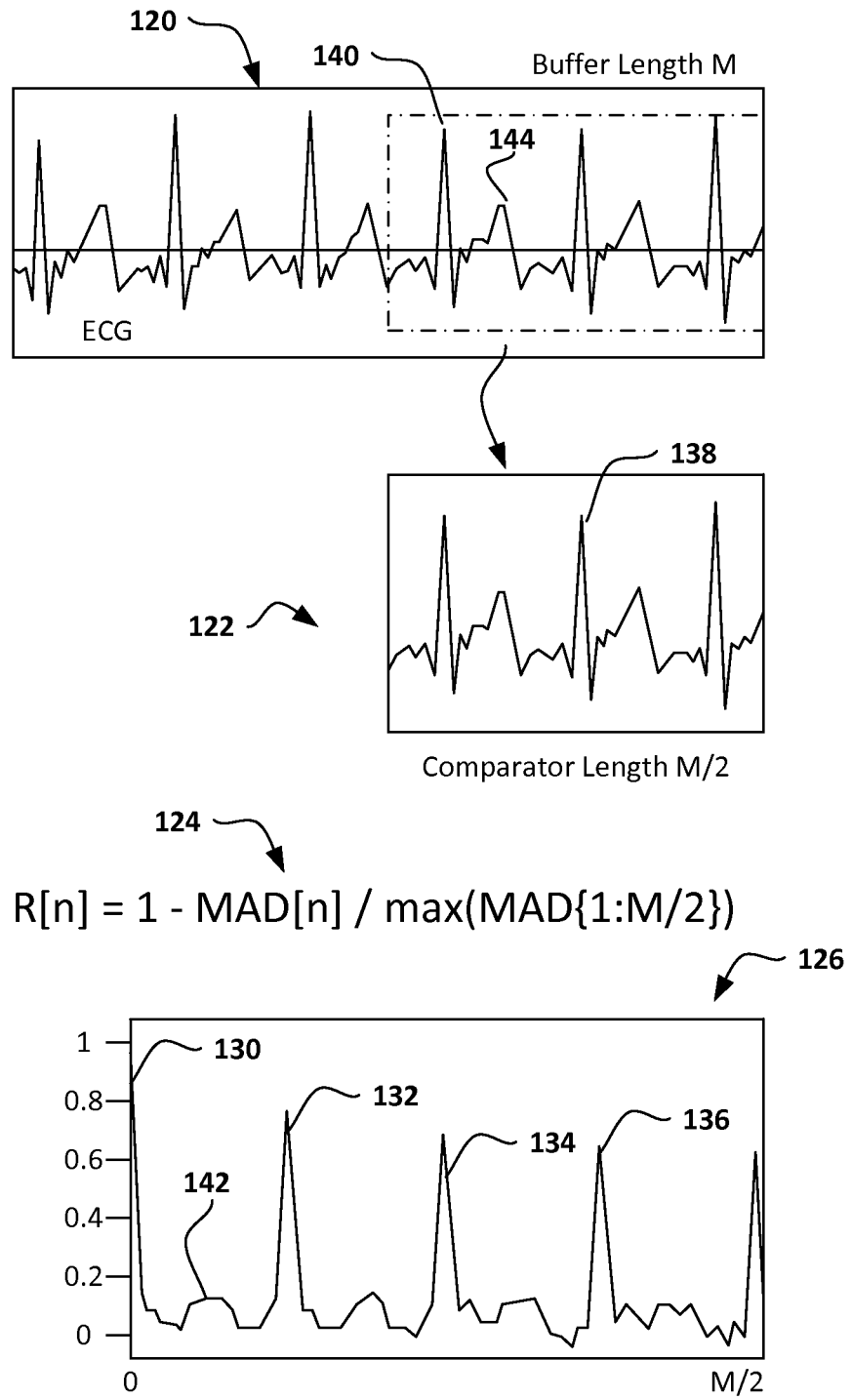

FIG. 3 shows an overall method for generating a cardiac rate estimate. A function "R[n]" is calculated. The function, R, may be, for example, a self-correlation function as illustrated in FIGS. 4-5, below. The function R represents a series of comparisons performed by calculating a relatively large number (50 or more) comparisons between a comparator that is a portion of a signal, and the overall signal itself, where the comparisons are performed by repeatedly shifting the comparator relative to the overall signal.

Figure 10:
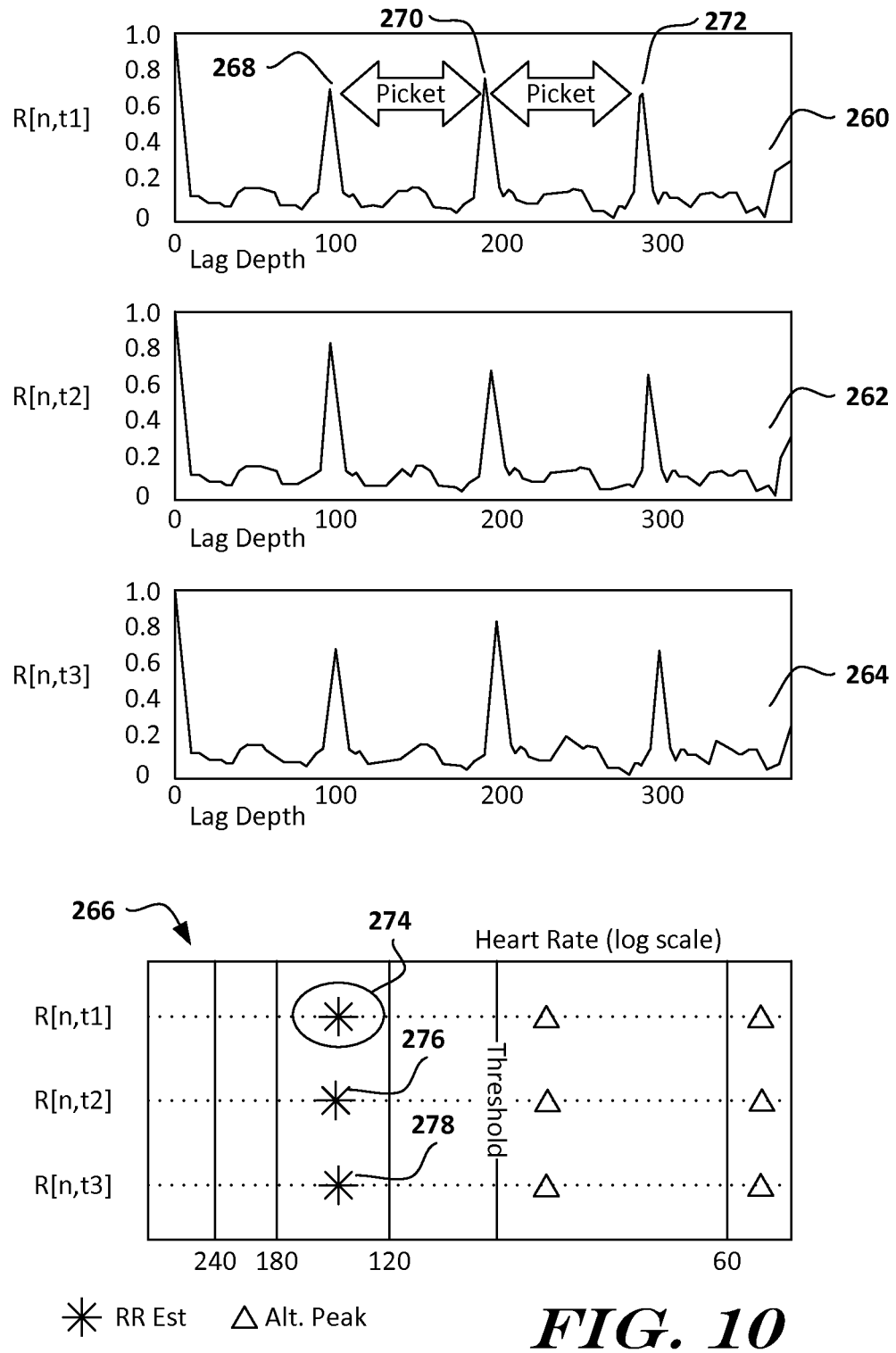
FIGS. 10-13 demonstrate several cardiac rate tracking steps using hypothetical examples.

R is discussed herein as a discrete function, rather than as a continuous function; in other examples, R may be a continuous function. In an example, R[n] may be a function that can be called periodically or it may be generated on a continuing basis. Briefly referring to FIG. 5, an illustrative R[n] as calculated at a selected point in time is shown at 140, based on a scrolling comparison of a comparator 122 to a buffer 120, the buffer 120 having length M and comparator a length M/2, providing R[n] a length of M/2. One could think of R[n,t], where n has values representing an individual calculation of R at a time t. For example, FIG. 10 shows three "R" functions—at each of t1, t2 and t3, R was calculated for n=0 to 400.

Figure 6:
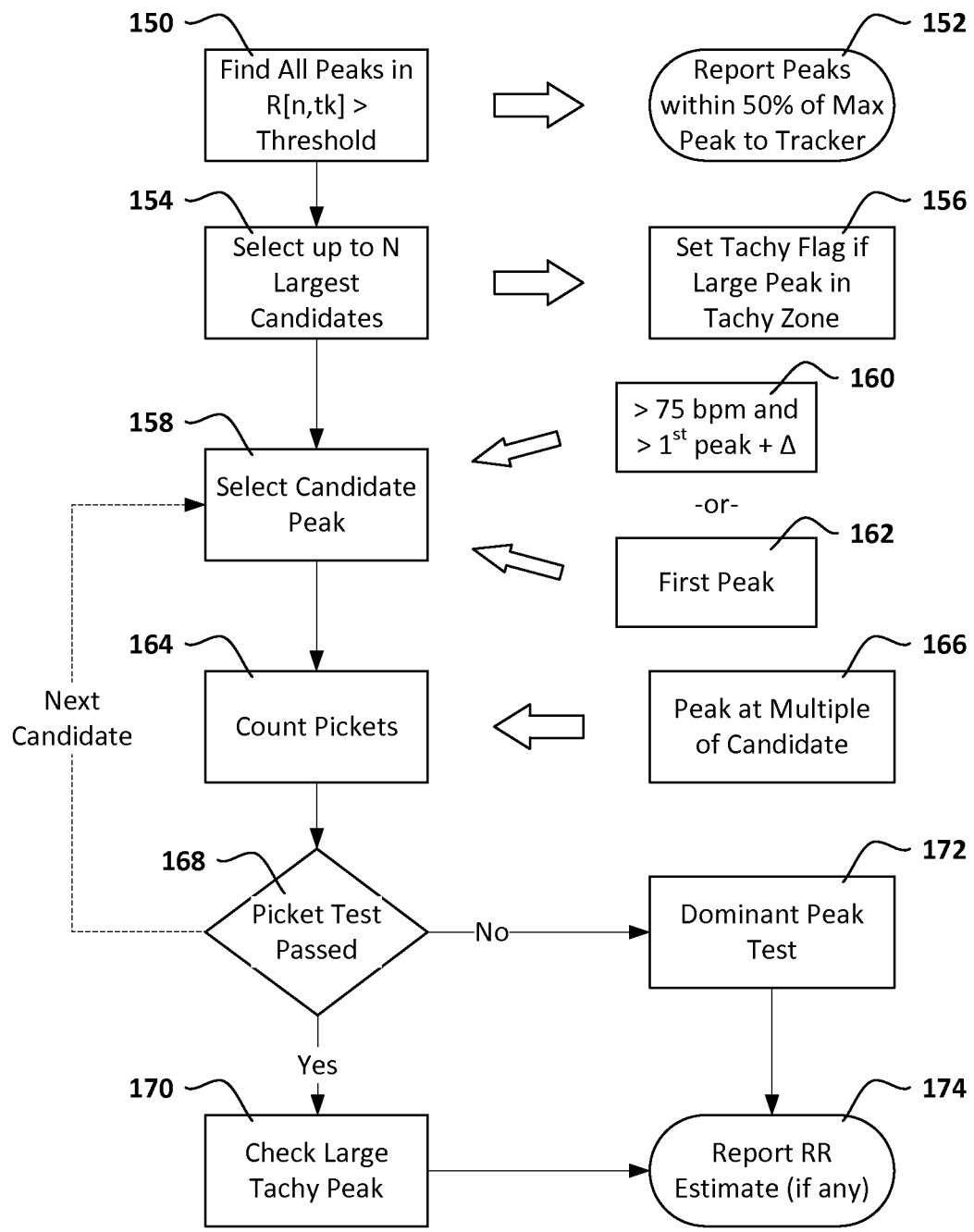
FIGS. 6-7 illustrate the analysis of R[n] peaks to identify candidate cardiac rates and a cardiac rate estimate.
Figure 7:
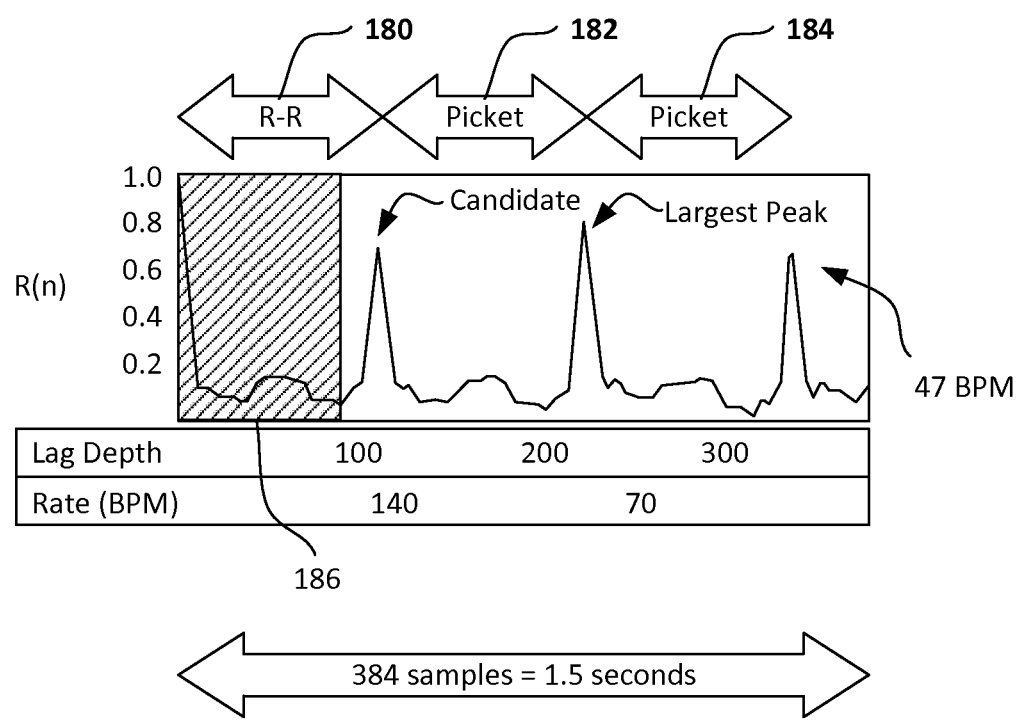

Using R[n] as calculated from step 60, a number of candidate peaks are identified at 62. FIGS. 6-7 provide examples of the identification of candidate peaks. Candidate peaks can be understood as representing a potential "rate" of cardiac events. A high match, as represented by a peak in R[n], suggests alignment of the cyclic electrical waveforms associated with a heart beat. For example, if a peak of R[n] occurs at n=90, and the sampling rate is 256 Hz, then the time between R[0] and the peak would be 90/256=352 ms. For this example, shifting the comparator back in time by 352 ms generates a relatively higher match between the comparator and the original signal. The 352 ms can be referred to as the lag depth, and if it truly is the interval between successive R-waves, it would correspond to 171 beats per minute (bpm).

Figure 8A:
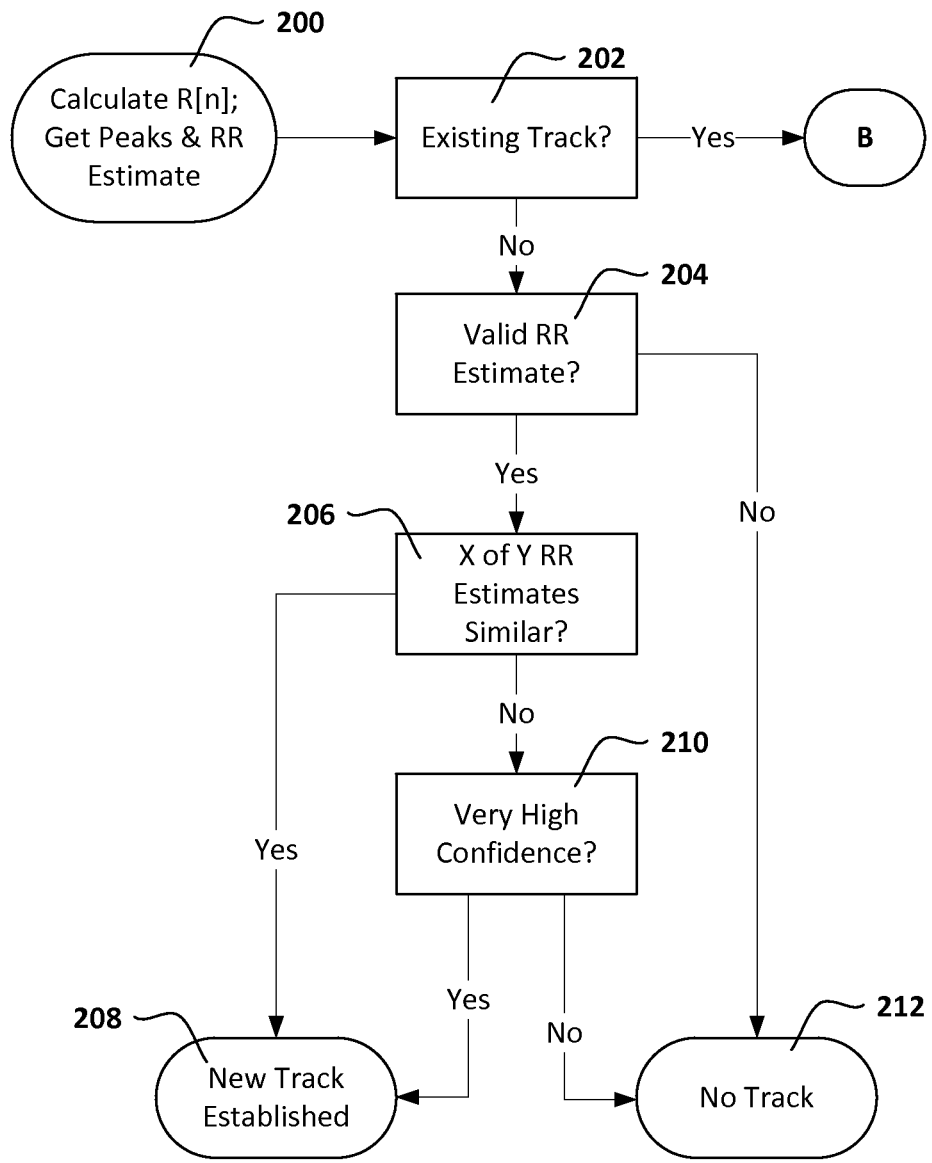
FIGS. 8A-8B illustrate one method of tracking cardiac rate.
Figure 8B:
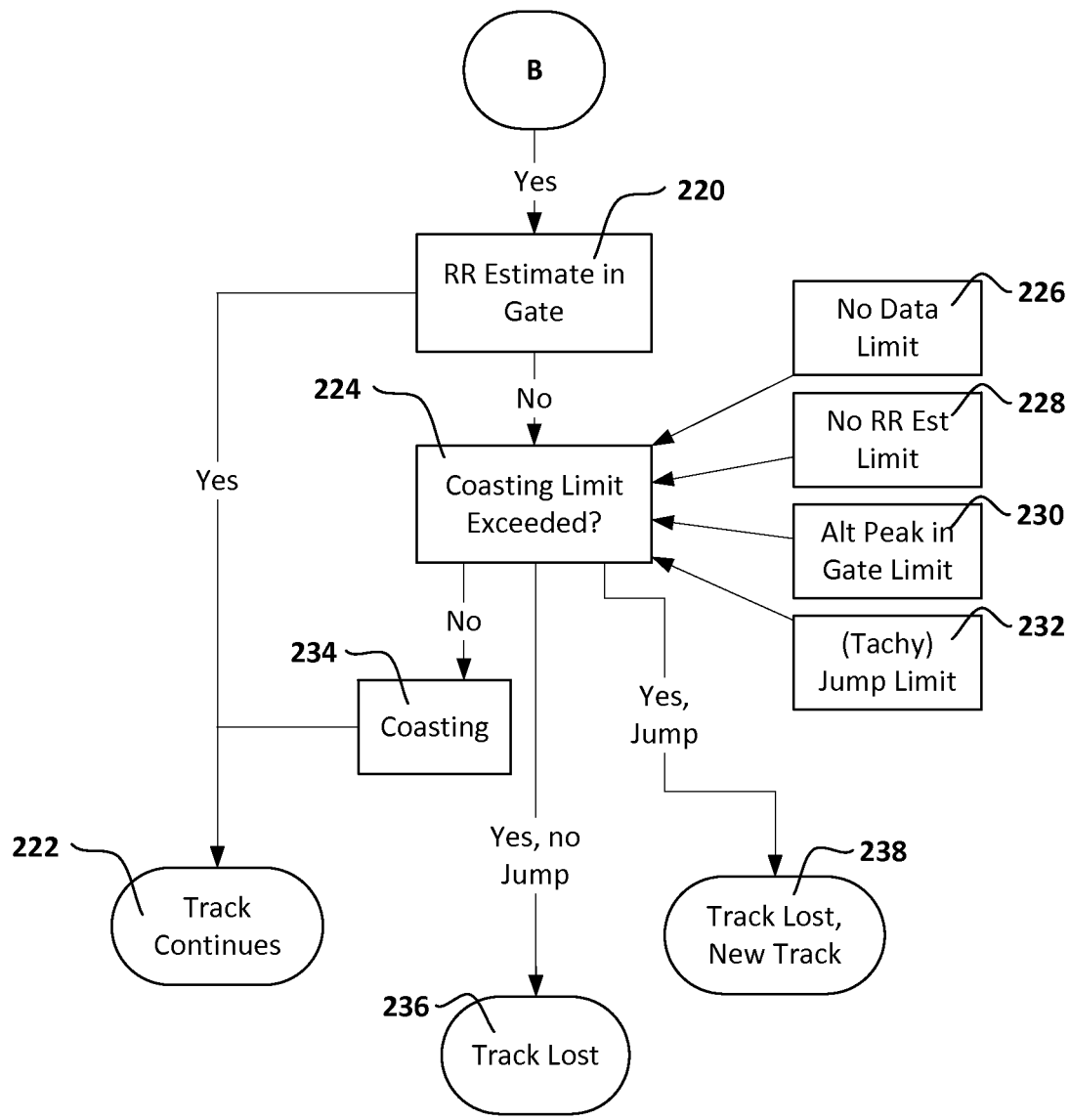
Figure 9:
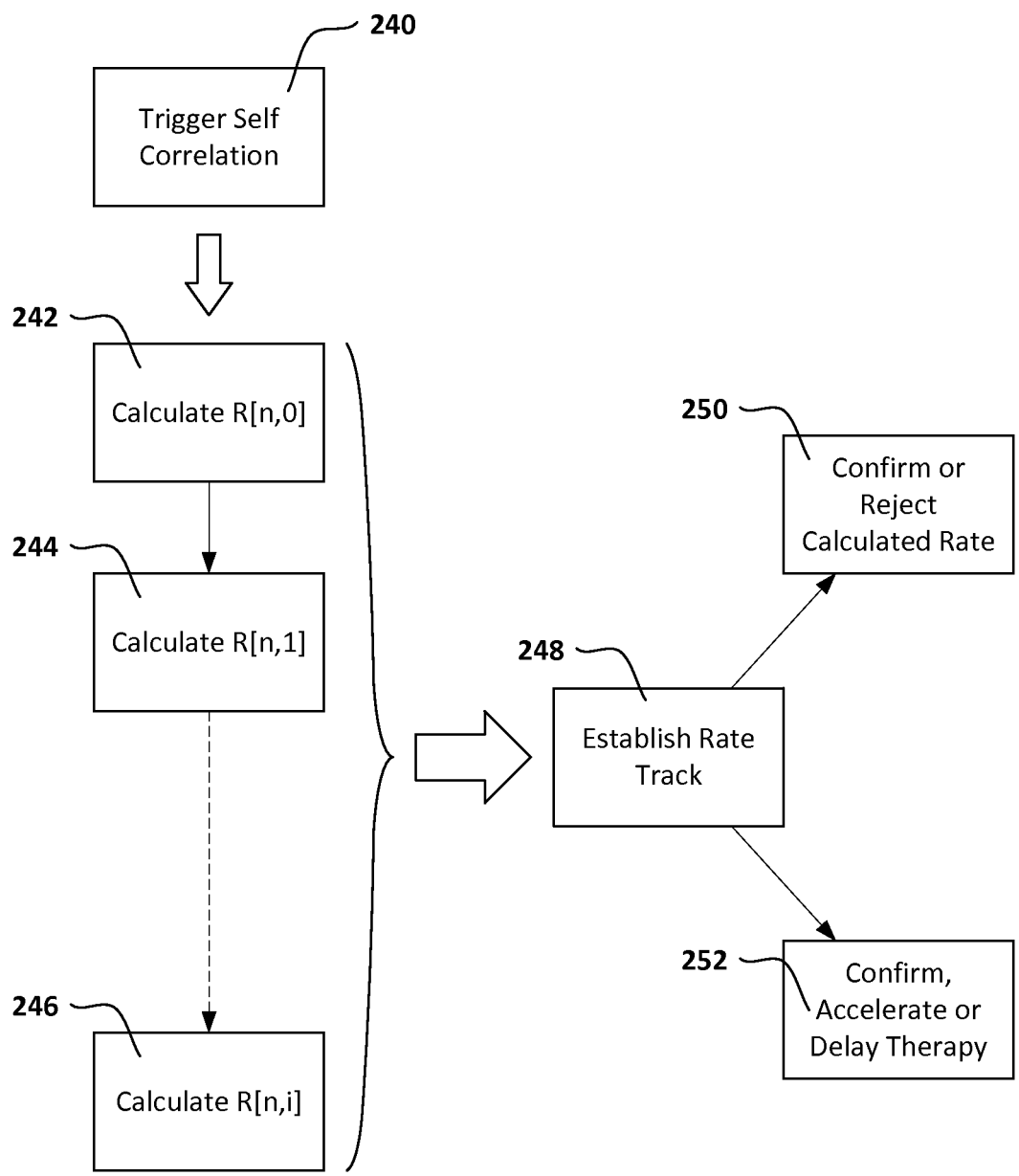
FIG. 9 illustrates tracking of cardiac rate over time.

Next the method determines whether a valid track exists, at 64. Tracking is the process of monitoring the outputs of the R[n] calculation and peaks therefrom to determine whether a high-confidence cardiac rate can be reported. FIGS. 8A-8B show an illustrative method of rate tracking FIG. 9 shows another approach to rate tracking.

If a track already exists, the method includes determining whether to confirm one of the candidate peaks, as shown at 66. If no track exists, then peak tracking is performed as shown at 68 to determine whether a new valid track can be declared. Next, following either 66 or 68, the method concludes the iteration shown by reporting a rate and confidence.

In some instances, no high confidence rate will be reported. For example, an atrial arrhythmia that is conducted to the ventricles may be characterized by unstable periods between ventricular depolarizations. As a result, the measured ventricular rate can be highly variable. When the ventricular rate is highly variable, R[n] may produce only relatively low peaks, or may not produce consistently similar peaks during iterative calculations. As a result, the output rate from the entire procedure may either be missing or may be reported with only low confidence at block 70. FIGS. 10-13 illustrate an example showing several iterations of the method of FIG. 3. FIG. 14 illustrates in a block flow diagram a manner of analyzing data generally consistent with FIG. 3.

In an example, the output rate and confidence can be used to confirm or call into question the cardiac rate as calculated using a more conventional process. For example, a device may use a default beat detection scheme in which the received cardiac signal, following amplification and filtering, is compared to a detection threshold. Some illustrative beat detection approaches are shown in, for example, U.S. Pat. Nos. 8,565,878 and 5,709,215, the disclosures of which are incorporated herein by reference. Crossings of the detection threshold can then be presumed to represent beats or R-waves, and various known methods can be used to identify and eliminate detection threshold crossings that are caused by noise or overdetections. See, for example, U.S. Pat. Nos. 7,248,921, 8,160,686, 8,160,687, 8,265,737, and 8,744,555, the disclosures of which are incorporated herein by reference.

The remaining detected beats or R-waves, and intervals therebetween, can be used to calculate rate. The present invention, in some embodiments, is used to double-check the rate calculated using such methods. Such double checking can be called as needed or provided on a continuing basis. For example, a double check may be performed to confirm rate prior to therapy delivery, or prior to preparations for therapy delivery. In some embodiments, the present invention may provide a rate estimate which can override the rate as calculated using other methods such as beat detection.

In another example, a double check may be performed to confirm accurate event detection as a way of verifying a sensing configuration where, if the sensing configuration is not verified, a sensing vector may be changed. In other embodiments, elements of the present invention can be used to provide rate calculation by default, or may be the sole source of rate calculations.

FIGS. 4-5 illustrate analysis of data using a self-correlation function and differentiate such analysis from ACF. FIG. 4 shows a sensed ECG signal at 100. The signal can be treated as a buffer of length M, as shown at 102. The calculation of R[1], R[2] . . . R[M−1] is illustrated at 104. Each calculation of R[n] is performed, in ordinary ACF, by multiplying (via dot product) a portion of the buffer and a portion of the comparator, with the comparator shifted in time relative to the buffer. The comparator itself is simply a copy of the original buffer. Because of the shifting in time, a correction factor is needed as shown at 106, since the dot product is calculated using fewer and fewer data points as the overlap is reduced in size with each successive calculation of R[n]. The shifting of the comparator may be referred to as a lag depth. The full calculation can be quite burdensome for an implanted device given the large number of operations required. Several simplifications are provided to facilitate an implantable system-based analysis.

A first simplification is to replace the multiplication to calculate a dot product with subtraction. The absolute value of the subtraction result yields a Minimum Absolute Difference (MAD). Swapping the dot product out and instead using MAD will reduce the number of required calculations by an order of magnitude or more, with minimal reduction in accuracy.

Next, to eliminate the correction factor for overlap 106, the buffer 110, having length M, is divided in half, to provide a sample portion M/2 and an available lag depth 114. Then the iterative comparisons identify the area of difference between the sample 112 and the buffer 110. As shown at 116, the result is M/2 total comparisons from a lag depth of zero to a lag depth of M/2.

An additional simplification may be performed in some embodiments by compressing the input data. For example, a system may perform analog-to-digital conversion of the cardiac signal at a rate of 256 Hz. The calculation of R[n] maybe performed on a limited or compressed version of the original signal, reducing the number of calculations again (though at the cost of calculations needed for downsampling, which may already be performed to facilitate data storage).

In a dynamic example, the sampling rate itself, or degree of compression of sampling rate, can be adjusted in light of the detected cardiac rate from one or more preceding iterations. For example, if a given calculation finds a relatively high cardiac rate, the uncompressed version of the original signal may be used, while if a calculation finds a relatively low rate, a compressed version of the original signal may be used instead.

Turning to FIG. 5, an example calculation of R[n] at a particular point in time is shown. The ECG is shown at 120, as stored by a buffer having a length M. The comparator for the self-correlation is shown at 122, and comprises the half of the buffer 120 having the most recently detected samples. Preferably, the length of M is enough such that at least 2 beats will fit within the comparator during benign rate (such as 60 bpm). Thus in an illustrative example, the buffer 120 has a length of about 4 seconds and the comparator 122 has a length of about 2 seconds. Another example has a buffer 120 length of about 2 seconds and a comparator 122 with a length of about 1 second. Other sizes may be used. In some examples, the invention is characterized by having a buffer large enough to ensure at least two cardiac cycles occurring at a defined lowest needed rate would be captured, where the lowest needed rate may be in the range of 60-120 bpm. In further illustrations, the buffer length could be from 1.5 to 6 seconds and the comparator length is between 750 milliseconds and 3 seconds. In the examples shown herein, the comparator is half the length of the buffer; in other examples, the comparator may be between one-tenth to one-half of the overall buffer length.

A number of additional adjustments are contemplated. In some examples, the length of the buffer and/or the length of the comparator may be adjusted in light of an estimated heart rate or a history of heart rates. For example, at slower heart rates, the buffer and comparator lengths may be too short to capture multiple cardiac cycles, which is desirable to obtain an accurate result. Therefore, a dynamic approach may be adopted in which the buffer and comparator lengths are adjusted in light of a one or more previous rate calculations, to a longer length with slower heart rates, and a shorter length at higher heart rates. To reduce power consumption, the periodicity with which the overall function is called may be adjusted as well so that the buffer length does not cause data to be analyzed more than twice, for example. In specific examples, the buffer length can be at least twice, or thrice, the inverse of the cardiac rate, and the period at which the function is called is selected to be equal to the inverse of the previously detected cardiac rate or an average of several rate preceding rate calculations.

In another example, a longer buffer and/or comparator period may be selected for use under certain device states. For example, following delivery of a high-voltage therapy (defibrillation or cardioversion, for example), a longer buffer and/or comparator can be selected. In another example, if a noise flag is provided (for example by identifying a period or set of noisy event markers such as defined in U.S. Pat. No. 7,248,921, which is incorporated herein by reference), a longer buffer and/or comparator may be selected. For these long/short buffer/comparator examples, some embodiments may set a default length of a two second buffer and one second comparator, and switch to a four second buffer and two second comparator, for example. Other durations and types may be selected.

In another dynamic example, if one or more indicators of variable intervals between cardiac R-waves are identified, a longer buffer and/or comparator length may be selected. For example, if the P-wave can be observed, absence of the P-wave suggests an atrial arrhythmia which can cause variable R-R intervals. For another example, if a correlation waveform analysis, in which QRS complexes are compared to one another or to a template, shows the morphology of the cardiac signal is unchanging, but intervals between R-waves as calculated using ordinary R-wave detection, for example, again, the combination suggests an atrial arrhythmia. Other markers are noted, for example, in U.S. Pat. Nos. 8,457,737 and 8,942,802, the disclosures of which are incorporated herein by reference. Using one or more of these markers, then, the buffer and comparator lengths may be increased by 50% or 100% over standard lengths noted above (such as 1 second/2 seconds) when atrial flutter or atrial fibrillation are suspected.

As shown at 124, an MAD function is applied in this example, and is then normalized using the maximum of the MAD across all of the comparisons made for a particular iteration of R[n]. This yields a result that is graphed at 126. The resulting graph includes a peak at 130, which corresponds to the zero lag depth calculation, during which the MAD would be zero, giving an output of 1. The next peaks 132, 134 and 136 each correspond to points in time where the MAD is calculated while the R-wave peaks in the comparator are aligned with a set of R-wave peaks from the buffer. For example, if peak 138 of the comparator is aligned with peak 140 of the buffer, this would also align the adjacent peaks if the R-wave intervals are similar, giving a small absolute difference at that particular alignment. In the analysis, the zero lag depth calculation is typically ignored.

Other peak alignments between the comparator 122 and the buffer 120 may generate lesser peaks in R[n]. For example, peak 142 occurs when peak 138 of the comparator is aligned with the T-wave at 144. This positioning creates a smaller MAD output which, once normalized using formula 124, would generate a noticeable but small peak in R[n]. Normalizing with a formula such as that at 124 facilitates comparison to fixed thresholds to distinguish between relative peaks within a poorly matching signal, and meaningful peaks showing alignment and matching between the buffer and the comparator.

The R[n] function may be calculated periodically. In one example, because the buffer and comparator take up fairly large blocks of time, such as more than one second or even two seconds, there is no need to continuously recalculate R[n]. For example, the period between recalculations of R[n] may be approximately the duration of the comparator, or, in another example, approximately half the duration of the comparator. For example, if the comparator length is 2 seconds, the buffer may be 4 seconds long and the calculation of R[n] could be performed at one second intervals. Thus, every second, the buffer would be updated and the comparator reformed, and the sequence of comparison and time shifting would be repeated. FIG. 10, for example, shows repeated calculation of R[n] at t1, t2, and t3, hence, R[n,t1], R[n,t2], and R[n,t3] are shown at 200 of that figure. The illustrative examples in the various Figures herein suggest the use of an asynchronous calculation of R[n]. These are asynchronous insofar as the calculation is not linked or synchronized to a beat detection performed by some other method. Other embodiments may instead use a beat-synchronous update or recalculation of R[n]. A hybrid embodiment may update synchronously to take advantage of microprocessor/microcontroller wakeup caused by beat detection, but may limit calculation of R[n] to occur no more frequently than some desired metric. For example, calculation of R[n] may be beat synchronized at intervals of no less than one second. FIGS. 6-7 illustrate the analysis of R[n] peaks to identify candidate cardiac rates and a cardiac rate estimate. FIG. 6 shows the operation in a flow diagram, while FIG. 7 provides a graphic example.

In FIG. 6, beginning at block 150, the method starts with the identification of any peaks within R[n,tk]. In this example, peaks that are within 50% of the largest peak and that meet some minimum size criteria are reported forward to a peak tracker, as indicated at 152. Tracking may be performed as shown below in FIGS. 8A-8B and 9, for example.

A set of largest candidates are then selected, as indicated at 154. In an illustrative example, a threshold may be set within the scaled calculation of R. For example, using the formula 124 in FIG. 5, the threshold for candidate peaks may be set at R=0.3, such that in order to be considered a candidate, a peak must be larger than 0.3 times the largest peak. The largest peak will always occur at R[0], as that is when the comparator and buffer are perfectly aligned and thus R[0]=1. Any subsequent peak greater than 0.3 may be a candidate peak. In an example, up to five of the largest peaks greater than 0.3 (excluding the peak at R[0]) are treated as candidates.

As shown at 156, if any of the largest candidates have a lag depth which would place the candidate in the "tachy zone", a tachy flag is set. A candidate peak is in the "tachy zone" if the lag depth of the peak is relatively small. This may be identified by asking whether there is a peak at R[nt] where nt is less than a tachy threshold. For example, if the tachy zone flag is to be set for candidate peaks suggesting a rate above 160 bpm, and the sampling rate is 256 Hz, then a peak at n<96 is in the tachy zone, since the peak occurs with a lag depth of less than 375 ms equating to a rate above 160 bpm. The tachy flag, if set, indicates that the analysis suggests possible tachycardia, regardless the rate it ultimately concludes is most likely correct.

Next, a first candidate peak is selected as shown at 158. Either of two rules for finding the candidate peak can apply: a peak having a lag depth that allows a rate to be found that is greater than 75 bpm and which is larger than the first-in-time peak by a chosen limit, delta, can be chosen, as shown at 160 or, otherwise, the first-in-time peak of the candidate peaks is chosen, as shown at 162. The first-in-time peak is the candidate peak having the least lag depth. The first rule, at 160, allows a peak which is significantly larger than the first-in-time candidate peak to be selected, as long as it is above a rate threshold. In the example, the rate threshold is at 75 bpm; other thresholds may be used.

In the illustrative example, the combination of 160 and 162 ensure that peaks associated with higher rates will be analyzed first and, to this extent, biases the method to seek out higher rate candidates. A bias toward higher rates may be desirable to minimize the risk of heart rate underestimation in the presence of a tachyarrhythmia.

Next, the candidate peak is analyzed by looking for and counting "pickets", as shown at 164. The pickets are peaks at multiples of the lag depth of the candidate peak. FIG. 7 shows an example of pickets. A first peak is found at a lag depth of 110 samples (corresponding to 140 bpm sampled at 256 Hz). This lag depth gives an R-R interval as shown at 180. Two pickets can be identified by observing additional peaks at lag depths of 220 samples and 330 samples, which are multiples of the lag depth of the candidate. The pickets at 182 and 184 provide confirmation that the 140 bpm rate is likely the correct cardiac rate.

The counting of pickets can include an allowance for some variation in peak spacing. For example, the picket peaks should be equally spaced, within a maximum tolerance. The tolerance can be defined as a function of the calculated heart rate, or may be set in terms of milliseconds or samples (n). For example, if a first peak is at a lag of 80 samples (313 milliseconds at 256 Hz), a picket would be expected to appear between 75 and 85 samples away (293 milliseconds to 332 milliseconds). A narrower or wider tolerance may be defined in other examples.

It should be noted in this example that the largest peak is not the first selected candidate peak. There are two reasons why this is so: first, the largest peak is not sufficiently large relative to the candidate peak to meet rule 160. In an example, to select a peak other than the first peak as a candidate, the later peak needed to be at least 30% larger than the candidate (making delta relative), which is not the case here. In another example, delta may be a fixed value, such as 0.2 using the MAD formula 124 from FIG. 5.

Second, the largest peak is at a lag depth corresponding to a rate of 70 bpm, again not meeting rule 160. In the example, to select a peak other than the first peak as a candidate, the later peak needed to be at a lag depth corresponding to a rate greater than 75 bpm. Other thresholds may be chosen. The picket determination may require that the peaks used to establish subsequent pickets be among the largest N peaks or that each peak be larger than a predetermined threshold, such as a peak above 0.35 or 0.50 using the formula at 124 in FIG. 5.

Both of rules 160, 162 can be modified in other examples.

For illustrative purposes, FIG. 7 also illustrates a tachy zone 186. The tachy zone, in this example, covers a lag depth from zero to about ninety. This corresponds to an offset of up to ninety samples. In the illustration shown, 384 samples equate to 1.5 seconds, meaning a 4 ms sampling period. Ninety samples would correspond an RR Estimated Interval of 360 ms, equating to 167 bpm. As noted above, other settings for the tachy zone may be used.

Returning now to FIG. 6, the method proceeds by determining whether the picket test passed, as shown at 168. In an example, the picket test passes if there are at least two pickets identified relative to the candidate peak. In another example, multiple picket thresholds may apply depending on the lag depth of the peak under analysis. For example, in analysis with maximum lag depth N, a rule set may call for least two pickets for a candidate peak having a lag depth of less than N/3, and at least one picket for a candidate peak having a lag depth greater than N/3 and less than N/2. This relative approach accommodates the fact that, for a candidate peak having a lag depth between N/3 and N/2, only one picket is possible, as the second picket would be at a lag depth greater than "N" itself. Such relativity is optional, and may be managed, at least in part, using the dominant peak test discussed below.

If the picket test is passed, the method does a final check for any large peak in the tachy zone, as shown at 170. In some, limited instances, a large number of peaks may be reported during a chaotic tachy event. In such a case, the decision to select only "N" largest candidate peaks at block 154 could fail to choose as a candidate a peak in the tachy zone. Therefore the test at 170 looks for any peak in the tachy zone which is within 30% of the size of the largest peak, but which did not get identified as a candidate. Additional illustrative discussions of a large tachy zone peak test are provided in U.S. Provisional Patent Application No. 62/038,438, titled PEAK SELECTION FOR SELF CORRELATION ANALYSIS OF CARDIAC RATE IN AN IMPLANTABLE MEDICAL DEVICE, the disclosure of which is incorporated herein by reference.

If a large tachy zone peak is identified at 170, this peak is subjected to a picket test as well. If the peak chosen at 170 has pickets such that it passes the picket test, then the large tachy zone peak from block 170 is reported as the RR estimate at 174. Otherwise, as noted at 156, the tachy zone flag is set and the candidate peak that did pass the picket test at 168 will be reported as the RR estimate at 174.

In some examples, all candidates may be checked until one is found which passes the picket test and, if no picket test passes can be found for any of the candidate peaks, the method proceeds to block 172. Alternatively, only the first selected candidate peaks is subject to the picket test at 168, and, upon failing the picket test once, the method goes to block 172.

Upon reaching block 172, a dominant peak test is applied. The dominant peak test determines whether there is a peak that is 30% larger than all other peaks in R[n] (excluding the peak at n=0). If so, then that dominant peak is identified as the RR estimate.

The dominant peak test 172 may also be limited to passing when the identified dominant peak is at a lag depth corresponding to a rate below a preset threshold, such as 60, 75 or 90 bpm. The rate limit may be included in block 172 as an acknowledgement that there may be no pickets in the analyzed data for a low rate peak. This is so because the time span of the R[n] calculation may not be sufficient to produce a picket pattern for all heart rates, particularly lower heart rates with longer beat intervals.

For example, using a buffer of 3 seconds and comparator of 1.5 seconds length, the first picket for a peak at a lag depth of 800 milliseconds (75 bpm) would be at 1.6 seconds. Such a picket could not be identified given the buffer/comparator sizes, as the greatest lag depth is only 1.5 seconds given the 3 second/1.5 seconds buffer/comparator sizes. On the other hand, a dominant peak at a smaller lag depth, such as 500 milliseconds (120 bpm) would be expected to have two pickets in this scenario, and, absent any pickets, would not be treated as a highly likely RR estimate as there would appear to be less periodicity than would ordinarily be associated with a confident RR estimate. Additional discussion of a dominant peak test which may be used in at 172 is provided in US Provisional Patent Application No. 62/038, 438, titled PEAK SELECTION FOR SELF CORRELATION ANALYSIS OF CARDIAC RATE IN AN IMPLANTABLE MEDICAL DEVICE, the disclosure of which is incorporated herein by reference.

If an RR estimate is calculated via one of the three possible avenues—candidate peak passing the picket test (158-164-168), a large tachy peak (170) or the dominant peak test (172), the RR estimate can be reported out. A confidence grade can also be applied. In an example, three grades are available:

HIGH confidence if either
  Rate>TachyThreshold with 3 pickets and R>HCThreshold, or
  Rate<TachyThreshold with 2 pickets and R>HCThreshold;
MID confidence by default if no High or Low Confidence condition is met; and
LOW confidence if
  R<LCThreshold or
  1 or fewer pickets and Dominant Peak Test 172 not passed In this example, TachyThreshold can be set in a range calling for high rates, for example, over 150, 180 or 200 bpm. In some examples, TachyThreshold may be selected in light of the buffer and comparator size, in order to link to the quantity of pickets that could appear. The HCThreshold definition will be reliant on just how R is computed. In an example, given computation of R using the formula at 124 in FIG. 5, HCThreshold is set at 0.65. Likewise, LCThreshold will be defined in a manner closely tied to the computation of R. In an example also using formula 124 from FIG. 5, LCThrehsold is set to 0.35.

The confidence information may also be incorporated into the tracking steps shown in FIGS. 8A-8B. For example, switching from one track to another, or declaring a new track, may be accelerated in response to a high confidence rate, while such steps may be delayed for a low confidence rate.

In a Bigemini pattern, there are two alternating morphologies for ventricular depolarization or "R" waves. When a Bigemini pattern is analyzed using self correlation, it can be difficult to determine whether the output reflects R-wave and T-wave peaks, which alternate and have different morphologies, or two R-waves having a Bigemini pattern. Particular approaches to identifying Bigemini and/or jitter are shown in related U.S. Provisional Patent Application No. 62/038,437 filed on even date herewith and titled CARDIAC RATE TRACKING IN AN IMPLANTABLE MEDICAL DEVICE, the disclosure of which is incorporated herein by reference.

FIGS. 8A-8B illustrate one method of tracking cardiac rate. Starting at block 200 in FIG. 8A, any suitable manner of finding R[n], selecting a set of peaks and generating an RR Estimate are performed. The methods illustrated in FIGS. 4-7 provide various options for block 200. The tracking method begins by determining whether there is an existing or "active" track, as 202. If so, the method proceeds to B in FIG. 8B.

If there is no existing track, the method determines whether a valid RR Estimate has been generated, as shown at 204. If no valid RR Estimate can be had from the prior analysis, no new track will be declared, and the method terminates with no track at 212 and awaits a next iteration. If a valid RR Estimate was found, the method next determines whether X out of the last Y RR Estimates (or attempts) are similar, as shown at 206. For example, if 3 of the last 4 RR estimates are similar, the test at 206 would be met for an X/Y of 3/4. In one example, a 3 of 6 rule is applied at 206. If the test at block 206 is met, then a new track is established at 208.

If the test at 206 is not met, a new track may still be established on the basis of a single very high confidence rate calculation. The definition of very high confidence may vary. In one example, the HIGH/MID/LOW confidence rules applied above may be used, and any RR estimate that is calculated with HIGH confidence would be sufficient to meet the rule at 210. In another example, a separate threshold for the very high confidence rule at 210 may be set. In one embodiment, block 210 is met when R>0.85 in a system calculating R using the formula shown at 124 in FIG. 5. If the rule at 210 is met, a new track is established as shown at 208. Otherwise, no new track is set, as noted at 212.

Turning to FIG. 8B, a valid track exists, and it is determined whether the latest RR Estimate is within the Gate, as shown at 220. The Gate has a width, which can be defined in various ways. For example, the gate may be 40 milliseconds wide, or it may be 20 bpm wide. The Gate may be centered on a prior RR Estimate or average of 2-4 previous RR Estimates. In one illustration, the Gate is calculated by converting the most recent RR Estimate to bpm, and setting the upper and lower bound 10 bpm away. Thus, for example, if the most recent RR estimate is 400 ms, that converts to 150 bpm, and the Gate would be from 140 bpm to 160 bpm and an RR estimate between 429 ms and 375 milliseconds would be considered "in" the gate.

Gate width may also factor in rate variability. For example, the variability of a set of recent RR Estimates can be calculated by simply tracking how much change there is one from one estimate to the next. The Gate width may be increased if the rate appears to be highly variable in this example.

If the RR Estimate is within the Gate, the method declares the track continued at 222. The RR Estimate is also reported out.

If the RR Estimate is not within the Gate, then the Coasting rules are applied. Coasting takes place when a valid track has been identified/defined, but an iteration of the RR Estimate calculation fails to yield a result that meets the track definition. The use of Coasting allows the track to continue and passes over temporary disturbances such as noise or PVC, for example. Coasting avoids gaps in the output RR Estimate by holding the last known RR Estimate. Coasting can be particularly useful when a peak exists in R[n] but fails, for whatever reason, to otherwise pass the rigorous tests in the peak selector for identifying the a candidate peak as an RR estimate. Coasting is available to salvage the RR Estimate for such peaks, but only for a limited time.

In the illustrative example, Coasting is not allowed to continue indefinitely and a limit is applied, as shown at 224. If coasting is within its limits, the method continues via block 232 and continues on the track at 222. To limit coasting, various rules can be applied and each may have a different limit.

For example, as shown at 226, if no RR estimate or peaks are reported up from the calculation of R, there may be a first, "No Data" limit to the duration of coasting. In an example, the system will only allow a single iteration of "No Data" before declaring the track lost at 236. Such a "No Data" condition can occur, for example, if noise has interrupted sensing and none of the peaks in R[n] exceed a base threshold. A "No Data" condition can also take place if a polymorphic arrhythmia onsets, such that R[n] simply fails to have any significant peaks.

Next, there is a coasting state in which no RR Estimate is produced, as shown at 228, with this state also requiring that there not be any of the reported peaks in the gate, as shown at 230. Thus, block 228 covers one set of circumstances in which rate estimate is lacking and the track is not being confirmed, while block 230 covers a state in which there is a lower confidence confirmation of the track, whether or not an out-of-track RR estimate has been identified.

A fourth form of coasting can take place as part of a transition or "jump" to an alternate track, as noted at 232. In this instance the existing track continues until either an alternate track condition is met by having a "new" track declared using a similar determination as in 206 or 210 of FIG. 8A.

As can be seen from blocks 226, 228, 230, 232, there are different inputs to the coasting state, each of which comes with somewhat varying confidence levels. For example, confidence in the underlying track or sensing reliability is low when no data is received 226, and not much better when there is no RR Estimate reported and none of the reported peaks fall within the gate 228. These two blocks 226, 228 may be combined for a single limit in the range of 1-3 iterations before the coasting limit is exceeded. Alternatively, block 226 may have a lower costing limit (1-2 iterations) while block 228 has an equal or higher limit (1-4 iterations), with a combined limit matching the higher limit (1-4).

The alternate peak in gate condition, at 230, is a much higher confidence condition, by suggesting that the track may still be valid, even if sensing a anomaly, such as noise, is present. This condition 230 may have a still higher coasting limit, in the range of 2-10 iterations or may be subject simply to an overall limit (in the range of 2-10 iterations) which would combine any coasting within any of 226, 228, 230 or 232.

Block 232, the Jump limit, is present to enable quick transition to a new track, without having to first wait for a declaration that the track is lost at 236 before assessing whether a new track exists. The Jump limit also prevents a shift to a new rate based on peaks that appear within an old, but no longer valid, track. When a coasting limit is met at 224 via the jump limit, the outcome follows a different path to 238. As a result, if the Jump limit is met, the method simply continues with a new track definition. To meet the Jump limit 232, in an illustrative example, the same rule as was applied at 206 may be applied to the new track. As noted at 232, the Jump limit may be applied just for high rate conditions, which are of greater concern generally than low rate conditions, using, for example, a limit in the range of 100-180 bpm, with 150 bpm being one example rate in particular.

The use of the Jump allows a quick transition to a higher rate RR Estimate, with a less stringent rule set when there is an existing track and a jump takes place. In the example, to declare a new track when no track has been identified would require a higher confidence in the new data than is required for the jump.

If the coasting limit is exceeded at 224, the track will be declared lost, as noted at 236. If the coasting limit is not exceeded, the coasting "state" can be recorded 234, with different coast states identified for each of the different coasting conditions 226, 228, 230, 232. While coasting, the track continues as shown at 222 until the next iteration is called.

FIG. 9 illustrates tracking of cardiac rate over time. There may be various triggers for performing self-correlation, as noted at 240. For example, self-correlation may be a default, continuing analysis called by an implantable system throughout the life of the system. Alternatively, self-correlation may be called in response to an identified potential condition necessitating treatment, such as an elevated rate condition. In one example, the cardiac rate may be calculated using conventional R-wave detection schemes (often by comparing the detected cardiac signal to a time varying threshold). If the identified rate crosses a threshold, the self-correlation methods may be initiated to confirm elevated rate. Thresholds may be set, for example, in the range of 100-180 bpm, or higher or lower, as desired.

In one example, a cardiac therapy system may use a number of intervals to detect (NID) approach or an X/Y filter to transition from unconcerned state into a therapy preparation and delivery state. For example, an X/Y filter may call for 18 out of 24 prior detected heart beats to be analyzed and considered treatable before therapy is delivered. For such a system, if X reaches a lower threshold, for example, 8/24, the self-correlation may be called to begin analyzing and confirming (or rejecting) calculated rates before the 18/24 boundary is reached. Similarly, if an NID approach is used, an NID threshold that is below a therapy boundary may be used to trigger the self-correlation analysis.

In another example, self-correlation may be called to periodically confirm sensing integrity by calculating a cardiac rate for comparison to other rate calculation methods/circuits. In some examples, the self-correlation shown in the present application may serve as the sole estimator of cardiac rate in an implantable device.

Once the analysis is triggered at 240, the self-correlation is performed at intervals, such that R[n,t] is calculated for each of t={0, 1, . . . i}, as shown at 242, 244, 246. From this series of calculations, a rate track is sought and, if possible, established as shown at 248. The analysis may confirm or reject a calculated rate, as shown at 250.

In addition, the analysis may be used to confirm, accelerate or delay therapy delivery, as noted at 252. Returning to an above example, if the self-correlation is called once the cardiac rate identified by conventional R-wave detection crosses a threshold, if self-correlation confirms an elevated heart rate requiring therapy, a therapy threshold may be lowered. For example, if a system uses an X/Y counter set to 18/24, the counter may be reduced to 12/16 if self-correlation confirms a very high rate prior to the X/Y counter condition being met. In another implementation, the self-correlation RR estimate can replace a conventionally calculated heart rate for a specified period of time, quantity of detected events, or until a next calculation of R[n] and analysis thereof is performed.

FIGS. 10-13 demonstrate several cardiac rate tracking steps using hypothetical examples. FIG. 10 illustrates the initiation of a rate tracking activity. The self-correlation function is calculated at each of times t1, t2 and t3, as shown at 260, 262 and 264. For purposes of understanding operation of this embodiment, a graph at 266 illustrates how the peaks of each R[n] calculation align with one another. Looking at R[n,t1], the graph at 260 illustrates that three peaks above the R=0.3 threshold were found, at lag depths of approximately 95, 190, and 285 samples. Using the method of FIG. 6, these three peaks 268, 270, 272 would be reported out of the peak analysis.

Next, again using the rules shown in FIG. 6, the first peak 268 from R[n,t1] is chosen as a candidate peak. Pickets would then be sought. As illustrated, there are two pickets identified for candidate peak 268, to the additional peaks at 270 and 272. Thus the method of FIG. 6 would confirm that peak 268 provides the RR estimate, while each of peaks 268, 270 and 272 would be reported to the tracking engine.

The RR Estimate from R[n,t1] is shown in graph 266 at 274; the other peaks from R[n,t1] are also shown as alternate peaks. Likewise, RR Estimates result from the analysis of the other two calculations at R[n,t2] and R[n,t3], as shown at 276 and 278. Here, no track has yet been declared. As a result, each of the RR Estimates may be deemed to yield a medium-confidence rate estimate, until a track can be declared.

Figure 11:
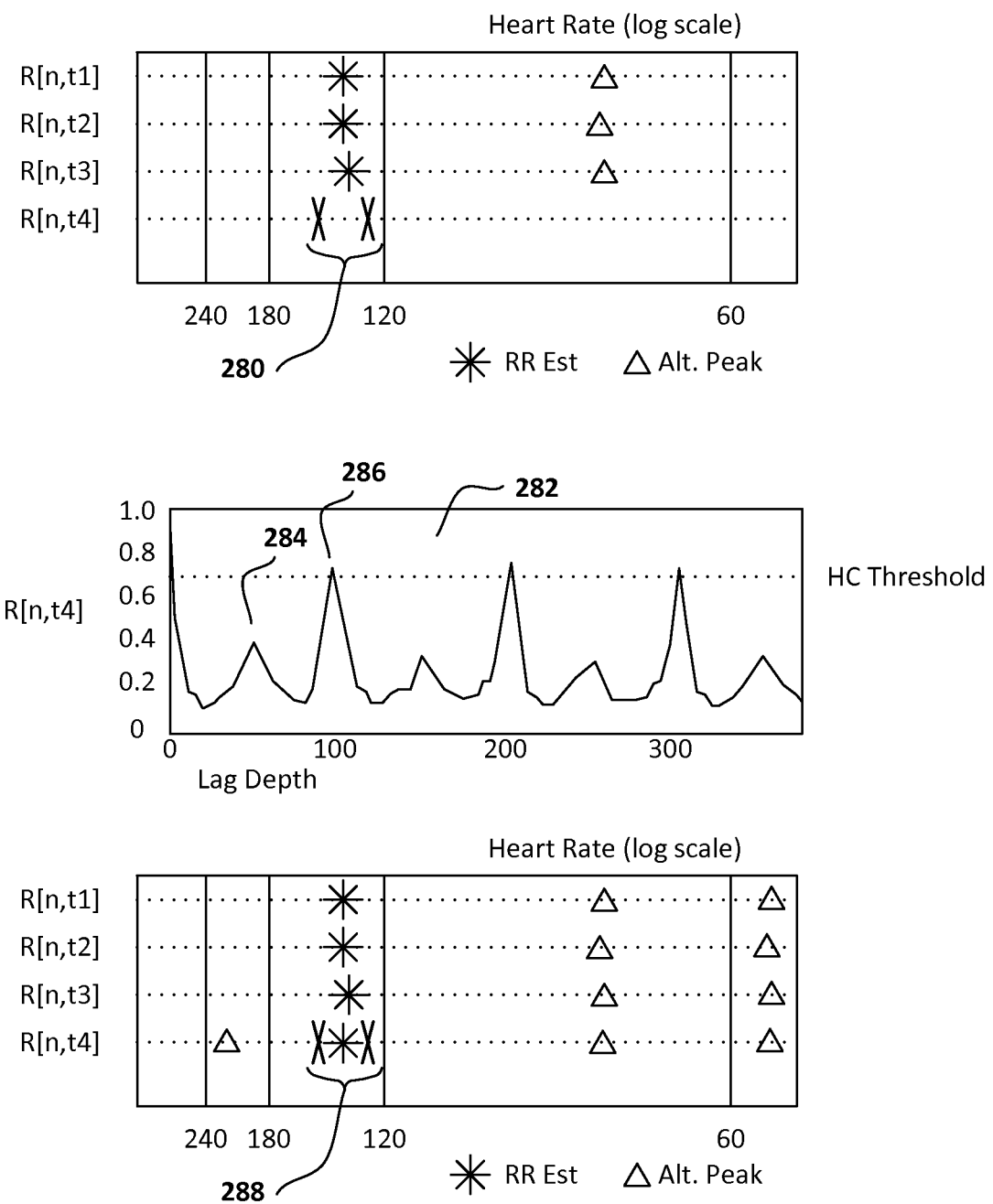

Turning to FIG. 11, the matching of the results for each of R[n,t1], R[n,t2] and R[n,t3] is sufficient to meet the track definition in FIG. 8B using a 3/6 rule. Therefore a track gate is shown at 280 for use in assessing the next iteration of the self-correlation, at R[n,t4]. The newly calculated R[n,t4] is shown graphically at 282. In R[n,t4], the peak associated with a T-wave comparison appears at 284 in addition to the much higher peak for the R-wave at 286. Again applying the rule set in FIG. 6, the first peak is at 284, and could be chosen if the rule at 162 in FIG. 6 controlled. However, the second peak at 286 is significantly larger than the first peak and appears at a lag depth that supports a rate greater than 75 bpm, meeting the rule at 160 in FIG. 6. Therefore peak 286 is selected for analysis, and is found as before to have two pickets (not shown) and is used to report out an RR Estimate. As shown at 288, the RR Estimate for R[n,t4] is within the gate.

It should also be noted that the peak 286 that is used for the RR Estimate exceeds an HC Threshold for high confidence. Therefore, the RR Estimate at 288 would then be used for rate reporting by the tracker, with high confidence.

Figure 12:
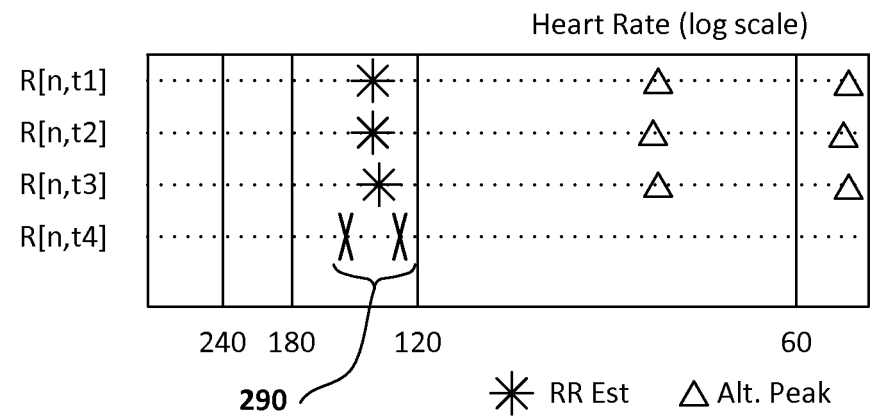
Figure 12:
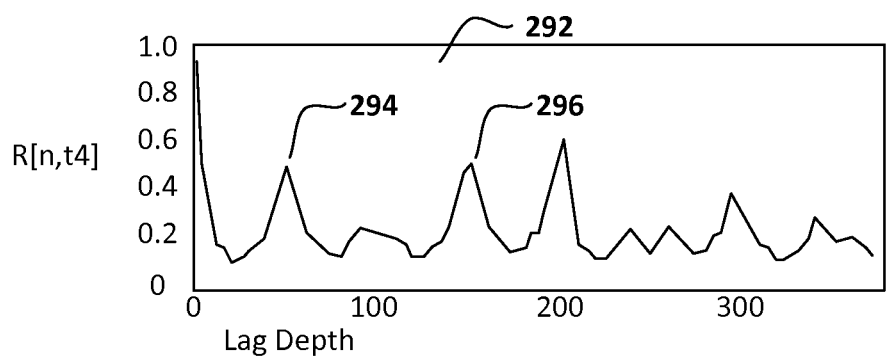
Figure 12:
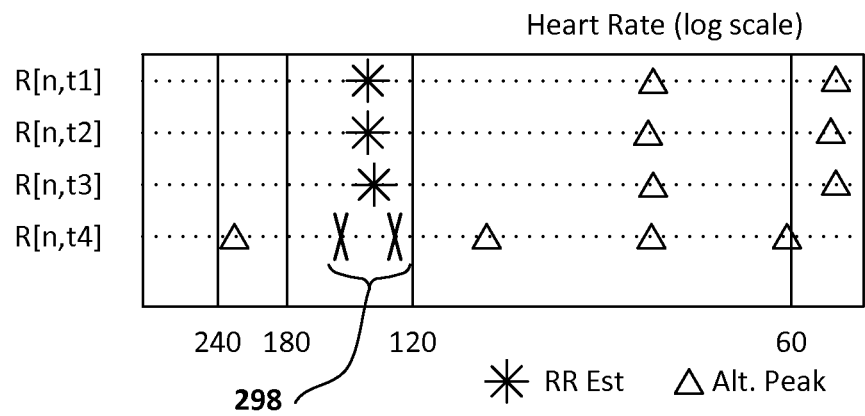

FIG. 12 presents a different scenario for the calculation of R[n,t4] after the track is established and gate is set at 290. Here, the output has changed dramatically from R[n,t3] to R[n,t4], as shown at 292. Using the rules of FIG. 6, the first peak 294 is chosen as a candidate peak, however, no pickets are found because the next significant peak, at 296, is too far away. There is also no dominant peak. As a result, no RR Estimate is calculated.

Looking at the updated overall graphic including R[n,t4], it can be seen that gate 298 is empty, without an RR Estimate or an alternate peak therein. As a result, for R[n,t4], the analysis is in a coasting state in FIG. 12. Because no RR Estimate could be calculated based on R[n,t4], a rate would not be reported to the Peak tracker. Because the track continues in a coasting state, an output rate estimate would be provided and, in an example, would be a value within the gate or could be the same as a previous output. Based on the empty gate at 298, the output rate estimate would be given a low confidence level.

Figure 13:
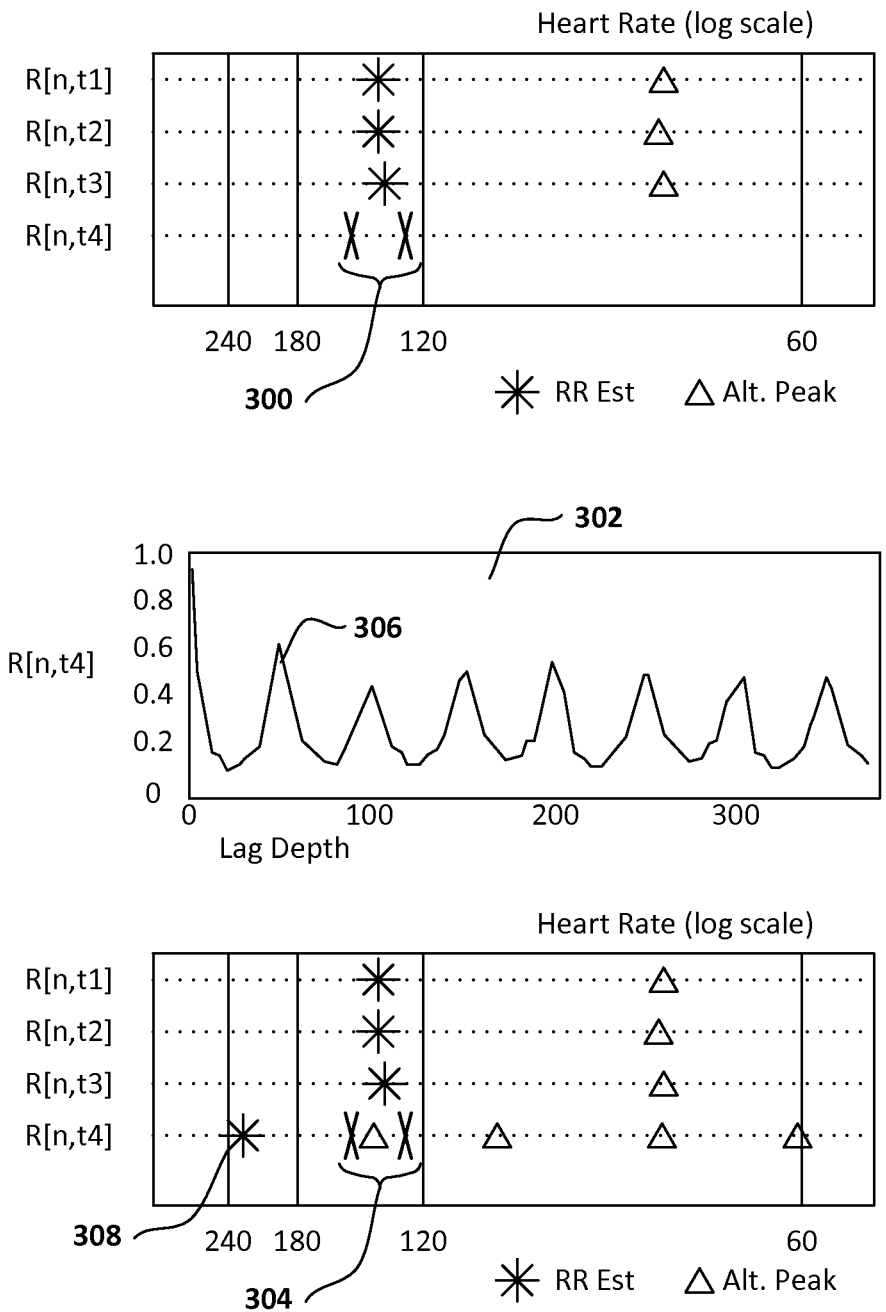
Figure 14:
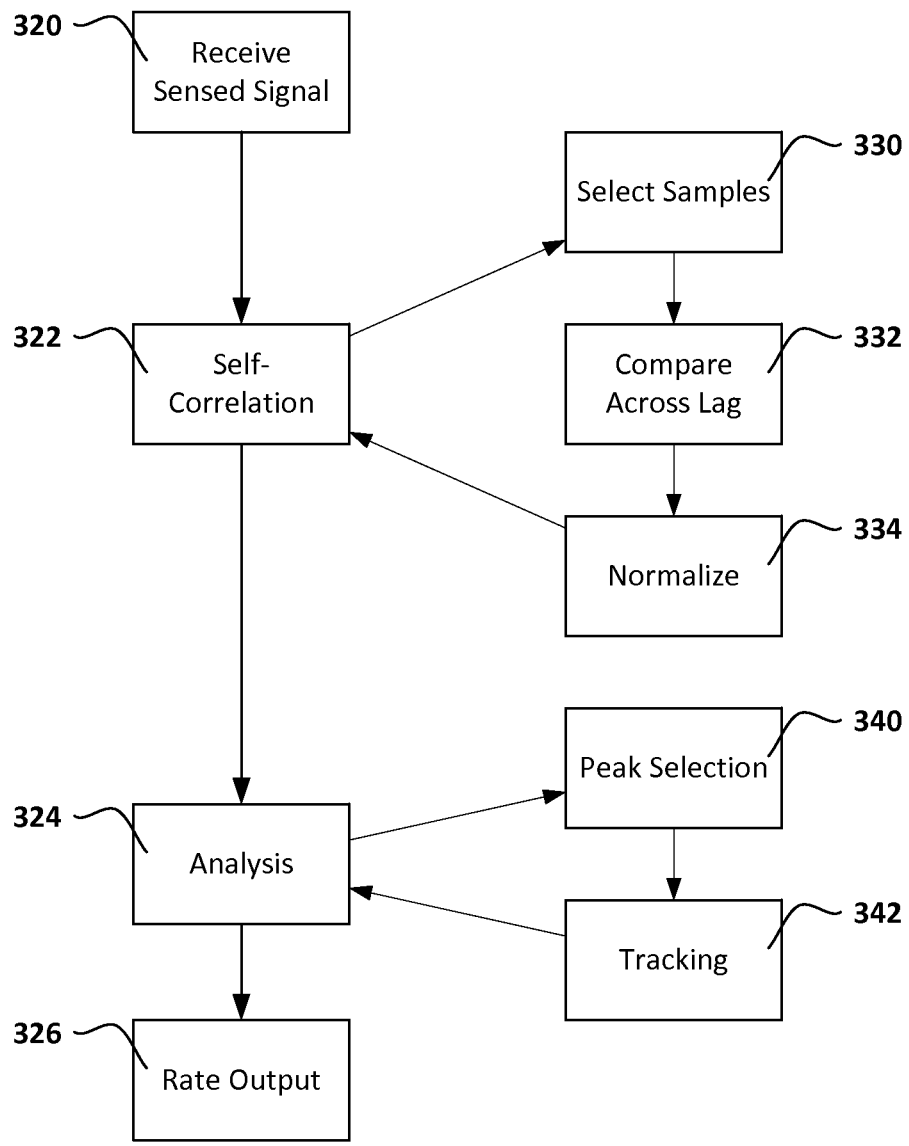
FIG. 14 is a block flow diagram showing an analytical approach.

FIG. 13 presents another different scenario for the calculation of R[n,t4] after a track has been established. Gate 300 is set for the analysis, however, R[n,t4], as shown at 302, does not identify a peak that sits within the gate, as shown at 304, as the RR Estimate. Instead, a peak 306 at a lesser lag depth is identified as the RR Estimate. Thus the RR Estimate 308 sits away from the gate 304, though one of the alternate peaks in R[n,t4] is within the gate.

Referring back to FIG. 8B, the event shown in FIG. 13 would trigger a coasting analysis using the tachy jump limit 232. Specifically, RR Estimate 308 is at a relatively short lag depth shown, in the example, as corresponding to a rate between 180 and 240 bpm. Given this is the first such RR Estimate, not enough information is available yet to declare a new track. This could be a momentary jump, or it could be the onset of a new rhythm. Until more data is received, the illustrative method will wait and coast with the track continuing. The output rate estimate would continue to be within the existing track. However, because the RR Estimate is outside of the gate, any rate estimate would be reported with low confidence. A Tachy flag would be set based on the large peak in the tachy zone.

Additional scenarios relating to the tracking examples in FIGS. 10-13 are provided in U.S. Provisional Patent Application No. 62/038,437, and titled CARDIAC RATE TRACKING IN AN IMPLANTABLE MEDICAL DEVICE, the disclosure of which is incorporated herein by reference.

FIG. 14 is a block flow diagram showing an analytical approach. The general approach is shown on the left-hand side of the Figure, beginning with receiving a sensed signal at 320. A self-correlation is performed on the sensed signal 320, as indicated at 322. The self-correlation analysis generates a result which is subjected to further analysis, 324. In several examples, this all leads to a rate output, as noted at 326.

Within the self-correlation 322, the analysis begins with the selection of the sample sets to work with, as shown at 330. For example, first and second sets of data are selected, each set having a length. The first data set can have a length that is approximately half that of the second data set, and the second data set includes at least the first data set plus additional data.

The first and second data sets are then compared to one another, as shown at 332, across the available lag depth. In an example, if the second data set has a length 2N, then the first data set has a length N and the available lag is also N. One example uses approximately one second of cardiac signal for the first data set, and two seconds of cardiac signal for the second data set. In other examples, different ratios may be used between the data sets. For example, the first data set can have a length N, with the second data set having a length 3N, giving an available lag depth of 2N. In one example, the first data set has a length of about one second, and the second data set spans three seconds.

In several examples, the first data set length of about one second is optimized for true cardiac rates of 120 bpm and higher, since it will not contain two cardiac cycles for slower true cardiac rates. A longer first data set, however, increases the computational burden. In one example, the first data set covers 1.5 seconds and the second data set covers 3 seconds, optimized for 80 bpm and higher. Other set sizes can be used. The analysis may cross the entire available lag depth, or only some portion thereof.

The comparison 332, as discussed above, may be performed using a dot product but, more preferably, is performed using a subtraction method to reduce the computational complexity and burden. This process at 332 can yield an output R[n,t], where n=0 to the maximum lag depth, and t denotes the time stamp of the analysis. The "t" notation is included here because the function may be performed iteratively, for example, at 1-3 second intervals (or shorter or longer, as desired).

The total lag and sample sizes, in some examples, is selected to ensure at least two cardiac cycles will be included in the analysis when the cardiac rate is in a range of, for example, 60 beats-per-minute. For example, given a 256 Hz data capture, downsampled to 64 Hz, the total quantity of samples in the first data set could be 64 samples, and the second data set may have 128 samples, such that one second of data is compared to two seconds of data through a one-second lag depth.

Next, in some examples, the output of this comparison can be normalized, as noted at 334. Normalizing can include, for example, scaling the output of the comparison to a value between 0 and 1, in some embodiments, though the output scaling is generally an arbitrary function. Normalizing 334 may be linear in nature, or can be performed using squares or square roots to generate smoothing functions or other functions that highlight features of the comparison output. For example, a complex approach may take the square root of the outputs of the comparison 332, scale these to a range from 0-1, and then square the output. In some examples, a simpler approach is taken to normalize to the maximum of the comparison 332. In some examples, the normalization step 334 can be omitted.

Turning to the Analysis block 324, as noted in the various examples above, one approach is to include first a peak selection analysis, as shown at 340, to identify one or more peaks in the self-correlation function which can be identified as likely cardiac rates, and then a tracking analysis 342 to assess the output of several iterations of the overall analysis to yield an even more confident rate estimate. Tacking 342 may also aid in the maintaining of rate estimates in the face of extraneous inputs such as noise, allowing the interpolation of likely cardiac rate even when the received signal from 320 is poor.

The combination of peak selection 340 and normalization 334 can be linked together. In certain examples, normalization is done to a scale of 0 to 1, with the peak selection 340 configured to ignore peaks below 0.3, 0.25, or 0.2. While such values are useful for understanding the approach, in many systems normalization would be done to a range between 0 and N, where N is a power of 2. For example, if one byte of memory is used for R[n], this permits values between 0 and 255 for R[n], and normalization 334 could be performed to use a full byte. Peak selection 340 would use a scaled threshold. For example, if peak selection uses 0.3 times N as a minimum peak threshold, then for a one byte R[n], 0.3 times 255 would give a minimum peak threshold of 76.5, meaning a peak of 76 would fall below the threshold, and a peak of 77 would meet the threshold.

In other examples, the tracking block 342 may be omitted. In some examples, the analysis 324 may be greatly simplified, for example, to simply pick the largest of the peaks output in the self-correlation function.

Figure 15A:
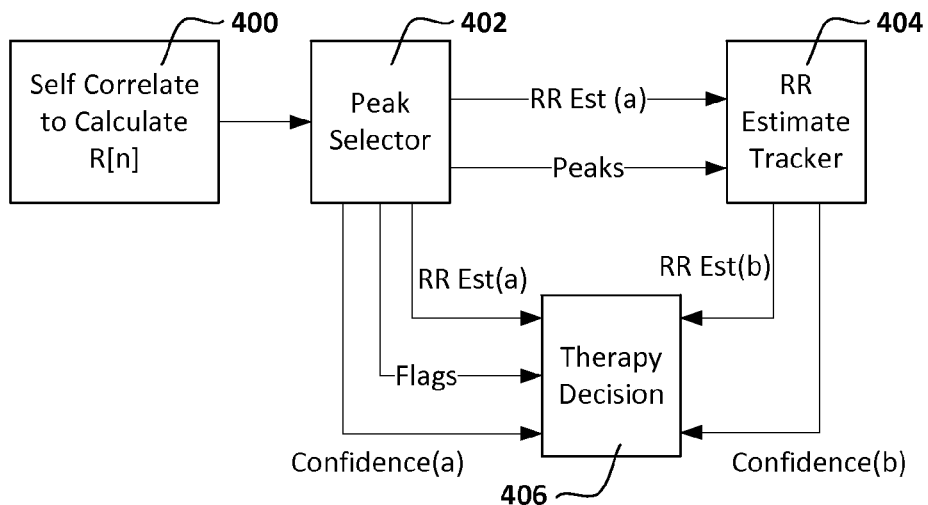
FIGS. 15A-15B illustrate different scenarios linking together the calculation of R[n], Peak Selector, Tracker, and Therapy Decision blocks.
Figure 15B:
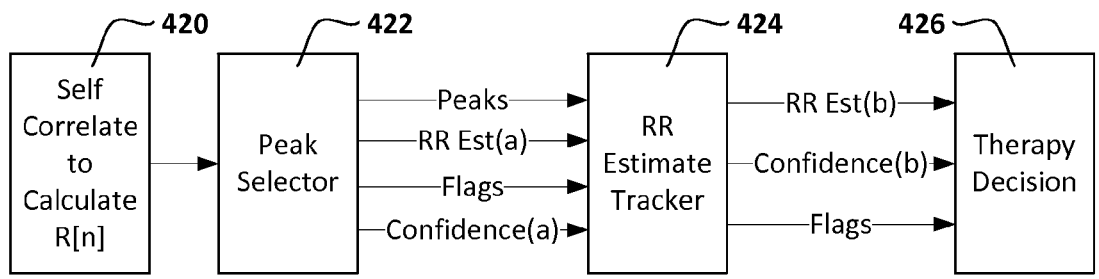

Illustrative examples may use the details provided in U.S. Provisional Patent Application No. 62/038,438, filed Aug. 18, 2014, and titled PEAK SELECTION FOR SELF COR- RELATION ANALYSIS OF CARDIAC RATE IN AN IMPLANTABLE MEDICAL DEVICE, in block 340. Another example uses the details provided in U.S. Provisional Patent Application No. 62/038,437, filed Aug. 18, 2014, and titled CARDIAC RATE TRACKING IN AN IMPLANTABLE MEDICAL DEVICE, in block 342. As noted above, the disclosures of these provisional patent applications are incorporated herein by reference FIGS. 15A-15B show several ways in which the R[n] Calculator, a Peak Selector, an RR Estimate Tracker, and a Therapy Decision can be linked together. In the example of FIG. 15A, the R[n] Calculator 400 reports the output of an R[n] calculation to a Peak Selector 402. The Peak Selector 402 provides an RR Estimate(a) and a set of Peaks to the Peak Tracker 404. The Peak Selector 402 also provides, in this example, the RR Estimate(a) to a Therapy Decision Block 506, along with any Flags arising out of the Peak Selector 402 analysis as well as a Confidence(a) indicator. The Therapy Decision Block 406 can use the RR Estimate(a) from the Peak Selector 402 as well as any Flags and the Reported Confidence(a) to determine whether a conventional rate estimate is likely correct or incorrect. The RR Estimate Tracker 404 reports an RR Estimate(b) and Confidence to the Therapy Decision 406.

For example, the Peak Selector 402 may identify an RR Estimate(a), but with low Confidence(a), while the RR Estimate Tracker 404 identifies a different RR Estimate(b) with higher Confidence(b), based on a secondary peak that meets an existing Track and which either has one or more pickets or is in a tachy zone, even if the reported RR Estimate(a) is not in the track. In that case, the Therapy Decision block 406 may ignore the RR Estimate(a) and instead adopt RR Estimate(b).

In another example, if the RR Estimate(a) is reported with High Confidence(a), but the RR Estimate Tracker does not find a peak in an existing track and reports it is coasting, using a preserved, prior RR Estimate and reporting a low Confidence(b), the Therapy Decision block 406 may adopt RR Estimate(a) over RR Estimate (b).

Thus, in the example of FIG. 15A, Therapy Decision block 406 is allowed to select from between RR Estimate(a) and RR Estimate(b), using the reported Confidences from each of the Peak Selector 402 and RR Estimate Tracker 404.

In the example of FIG. 15B, the R[n] Calculator 420 again provides its results to the Peak Selector 422. The Peak Selector 422 performs its function and provides Peaks, an RR Estimate(a), any set Flags, and a Confidence(a) to the RR Estimate Tracker 424. The RR Estimate Tracker 424 performs its function and provides an RR Estimate(b), Confidence(b) and any set Flags to the Therapy Decision block 426. Thus, in FIG. 15B, the RR Estimate Tracker determines a single output RR Estimate(a) with associated Confidence(b) to the Therapy Decision block 426.

One or more of the individual blocks in FIGS. 15A-15B may be separate pieces of hardware in a single system, though two or more blocks may be integrated in a single dedicated circuit. Alternatively, the separate blocks in FIGS. 15A-15B, may be separate functional blocks in a larger software structure. For example, given a stream (or stored stack) of data, a function call to Calculate R[n] 400/420 could be performed, followed by a function call to perform Peak Selection 402/422 given the output R[n], followed by a function call to Track RR Estimate 404/424 using the RR Estimate(a) and Peaks from Peak Selection, which may all be used as inputs (along with other data) for calling the Therapy Decision 406/426. In one example, blocks 400, 402 and 404 are provided on a dedicated circuit and the outputs of these blocks are provided to a processor or controller where the Therapy Decision process is performed.

In the embodiments shown in FIGS. 15A-15B (and other examples shown above and below), an RR Estimate can be considered an estimate of cardiac rate. Where a confidence measure is provided in association with an RR estimate and one or more peaks, such can be treated as one or more possible estimates of cardiac rate.

Figure 16:
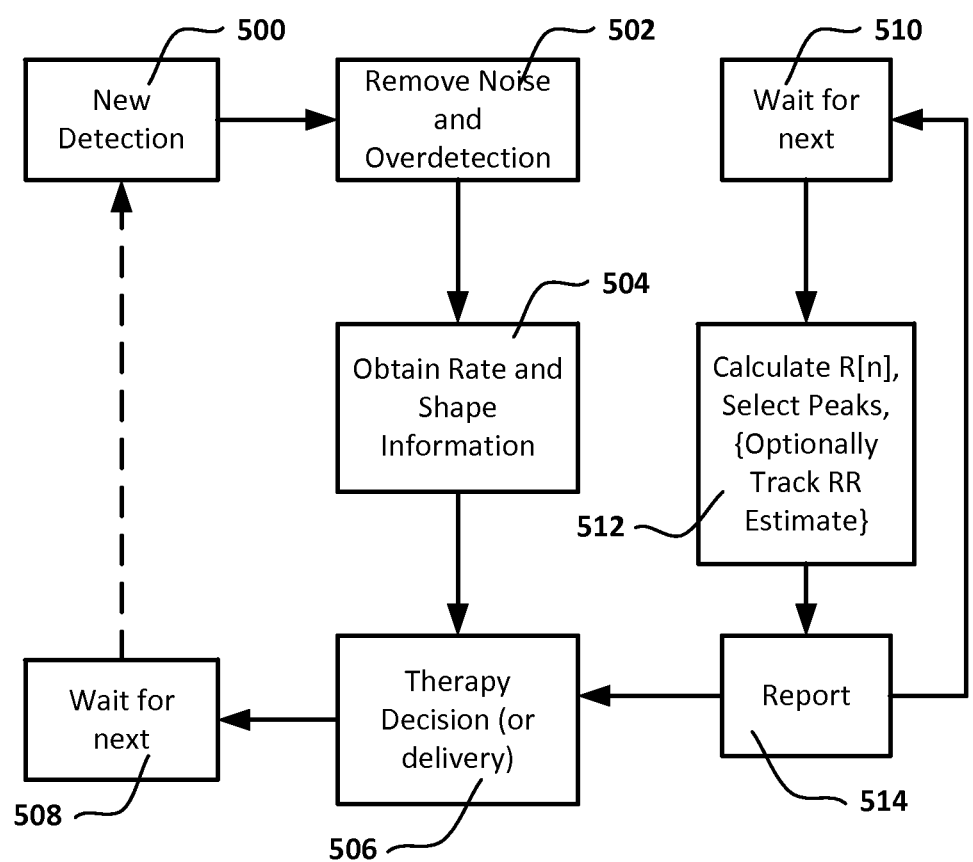
FIG. 16 is a block flow diagram for an overall method of cardiac signal analysis.

FIG. 16 illustrates an integration of two methods for identifying rate. A conventional rate method is illustrated using block 500, where R-waves are detected individually by comparing a detected signal to a threshold. Conventional R-wave detection may be used in block 500. Some illustrative examples appear in U.S. Pat. Nos. 8,565,878 and 5,709,215.

Detected R-waves are reported to a noise/overdetection removal block 502 which confirms the R-waves are likely cardiac events. Once the individually detected R-waves have been confirmed at 502, rate and shape (morphology) information are obtained 504 and provided to a therapy decision and/or delivery block 506. This conventional method then returns to a wait state 508 until the next R-wave detection.

The method also integrates a rate calculation using self-correlation, which can be called asynchronously (at fixed intervals, for example), or synchronously to the new detection 500, as desired. This wait state is depicted at 510. Upon activation, the self-correlation rate estimate is made using the combination one or more of calculating R[n], Selecting Peaks, and optionally Tracking an RR Estimate 512. A resulting RR Estimate is then reported at 514 to the Therapy Decision block 506, and the wait state 510 is again entered. The RR Estimate from block 512 may be generated using the tracking tools described above or, in some examples, a cardiac rate estimate may be generated directly from a peak selector that assesses a self-correlation function.

The therapy decision 506 may use each of these different calculations in various approaches to identifying whether therapy is needed. For example, one of the rates may be used to double check the other, or the rates may be compared to identify a match. If the rates do not match, additional analysis may be performed using, for example, additional sensing inputs, such as a motion sensor or blood pressure or oxygenation sensor. If the rates both suggest therapy is needed (whether matching or not), therapy functions may then be called. Other approaches are noted above.

In one example, if the dominant peak test is applied and met by a dominant peak, then therapy decision 506 may be configured to treat the estimated cardiac rate associated with the dominant peak as more reliable than a rate generated using an R-wave detection from block 500. In another example, a peak which passes the picket test may be treated in the therapy decision 506 as more reliable than a rate generated using an R-wave detection from block 500. In yet another example, the outputs of the peak selection may be treated as less reliable than the R-wave detection outputs until a track is declared via the methods of FIG. 8A-8B, and then only if the peak selection output falls within a defined track.

Still other examples may have multiple analytical courses depending on the status of the R-wave detection rate, tracking and peak selection outputs. For example, the following rules may apply in various examples:

If both R-wave detection rate and Self-Correlation Rate match and are high rates, the high rate is confirmed, suggesting tachyarrhythmia If R-wave detection suggests high rate but Self-Correlation Rate is lower, additional analysis is required (waiting time, detected event width or morphology analysis) before the high rate is treated as valid if either:
- the Self-Correlation Rate is based on a rate estimate falling within a valid track (the rate estimate being either a candidate or selected peak from peak analysis); or
- the Self-Correlation Rate is based on a selected peak that passes one of the picket test or the dominant peak test If R-wave detection rate is low, but Self-Correlation Rate is high, additional analysis (waiting time, detected event width or morphology analysis) is required before the high rate is treated as valid unless the Self-Correlation Rate is within a declared track and is based on a peak that passes the picket test (whether directly or via the large tachy peak test)

In another example, tracking is omitted and the following rules may apply:
- The rate calculated using R-wave detection is treated as valid if it is high and the Self-Correlation rate exceeds a tachy threshold (whether the rates match or not);
- The rate calculated using R-wave detection is treated as valid if it is high and the Self-Correlation test fails to meet either the picket test or dominant peak test;
- The rate calculated using the Self-Correlation test is treated as valid if it is lower than the R-wave detection rate and below the tachy threshold and either passes the picket test or passes the dominant peak test Other combinations are also possible within the scope of the present invention.

In one example, if the Self-Correlation analysis is called periodically, and if the Self-Correlation rate is calculated with high confidence, then the Self-Correlation rate takes the place of the rate calculated using R-wave detection until the next iteration of the Self-Correlation analysis. In a system using an NID or X-out-of-Y filter, then the Self-Correlation analysis rate can be treated as occurring repeatedly during the time period where the R-wave detection is replaced. For example, if Self-Correlation determines a rate of 180 beats-per-minute, and the Self-Correlation function is called at one second intervals, the NID or X-out-of-Y filter analysis would add three events at 180 beats-per-minute during the one second interval between iterations of the Self-Correlation analysis.

The therapy decision 506 may determine whether the cardiac rate as estimated by one or both of blocks 502/512 exceeds a therapy threshold using, for example, a direct calculation of one rate, or a calculation across several iterations using one or more of an NID or X-out-of-Y filter as discussed above. The therapy decision may combine rate with morphology (shape) information gathered from the cardiac signal. In some examples, the therapy decision 506 can set two or more rate boundaries, including one or more of a shock-only boundary, in which rates above a threshold are deemed necessitating high energy cardioversion or defibrillation shock, a VT zone in which a lower energy therapy such as anti-tachycardia pacing is applied, and a conditional zone in which additional analysis of a combination of shape elements (template matching, width, interval stability, amplitude, etc.) as well as rate is performed. The therapy decision 506 may integrate additional sensor inputs or inputs from separate devices, such as blood oxygenation, pressure, color, etc. measurements, measurements from a separate device such as a pressure monitor, leadless pacer, etc., or measurements from a position or movement sensor which can be separately provided in the patient's or integrated in a single device with the rest of the system that performs the self-correlation and other functions described above.

Various Notes & Examples

A first non-limiting example takes the form of an implantable medical device system (12, 14, 32, 34) configured for iterative analysis of cardiac signals comprising: a plurality of electrodes (16, 18, 20, 36, 38, 40, 42) for sensing cardiac signals; self-correlation means for generating a self-correlation function from the sensed cardiac signals, the self-correlation function having amplitudes as a function of lag depth; and analysis means for determining one or more estimates of cardiac rate using outputs of the self-correlation means; wherein the self-correlation means includes: sample selection means to select a first data set of the cardiac signal having a first length, N, and signal selection means to select a second data set of the cardiac signal having a second length, in which the second length longer than the first length, and the second data set includes the first data set; comparison means to perform repeated subtraction of the first data set from the second data set at a series of lag depths from approximately zero to approximately N, to generate the self-correlation function. A detailed example of the first non-limiting example is illustrated in the combination of FIGS. 1, 2 and 14, with electrodes shown in Figures and 2 in various locations and positions, and self-correlation means indicated in block 322, having selection means 330 for selecting the first and second data sets and comparison means 332 for comparing the data sets to one another, and analysis means illustrated at 324 generating a rate output 326. Certain variants on the first example may include having the second length be approximately twice the first length, and using an absolute area of difference calculation as the subtraction.

A second non-limiting example takes the form of a system (12, 14, 32, 34) as in the first non-limiting example, wherein the analysis means comprises peak selector means for identifying amplitude peaks in the self-correlation function and finding a first estimate of cardiac rate. FIG. 14 is illustrative, with peak selector means 340 as part of the analysis means 324.

A third non-limiting example takes the form of a system as in the second non-limiting example, further comprising normalizing means for scaling an output from the comparison means. FIG. 14 is illustrative, with normalizing means 334 as part of the self-correlation means 322.

A fourth non-limiting example takes the form of a system as in the third non-limiting example wherein the normalizing means is configured to scale the output of the comparison means to a scale between 0 and N; and the peak selector means is configured to ignore any peak less than 0.3 times N.

A fifth non-limiting example takes the form of a system as in any of the second to fourth non-limiting examples wherein the analysis means comprises tracking means for tracking outputs of the peak selector means to generate cardiac rate estimates using several iterations of the peak selector means outputs. FIG. 14 is illustrative, with tracking means 342 as part of the analysis means 324.

A sixth non-limiting example takes the form of a system as in any of the second to fifth non-limiting examples, wherein the peak selector means is operable to find the first estimate of cardiac rate by identifying the lag depth associated with an identified amplitude peak, converting the lag depth into a time interval, and calculating rate from the time interval. A seventh non-limiting example takes the form of a system as in any of the first to sixth non-limiting examples, wherein the first data set comprises data from the sensed cardiac signals covering approximately two seconds of data, and the second data set comprises data from the sensed cardiac signals covering approximately four seconds of data. An eighth non-limiting example takes the form of a system as in any of the first to sixth non-limiting examples, wherein the first data set comprises data from the sensed cardiac signals covering approximately one second of data, and the second data set comprises data from the sensed cardiac signals covering approximately two seconds of data. A ninth non-limiting example takes the form of a system as in any of the first to eighth non-limiting examples, wherein the self-correlation means is configured to first down-sample the sensed cardiac signals prior to the subtraction to reduce computational burden.

A tenth non-limiting example takes the form of a system as in any of the first to ninth non-limiting examples, further comprising decision means for determining whether cardiac therapy is needed. FIG. 16 is illustrative as including a therapy decision means 506.

An eleventh non-limiting example takes the form of a system as in any of the first to tenth non-limiting example, further comprising R-wave detection means for detecting R-waves in order to identify a cardiac rate therefrom, wherein the decision means is configured to select from a cardiac rate estimated using the R-wave detection means, and a cardiac rate estimated using the self-correlation function. FIG. 16 is illustrative as including R-wave detection means 500, 502, 504 for detecting R-waves and identifying a cardiac rate therefrom, with therapy decision means 506 taking rate information from both the R-wave detection 500, 502, 504 and self-correlation 510, 512, 514 and making a therapy decision.

A twelfth non-limiting example takes the form of a system as in the eleventh non-limiting example, wherein the R-wave detection means is operable to compare sensed cardiac signals to a time-varying threshold in order to generate detections of heart beats, such that cardiac rate can be calculated by identifying intervals between detected heart beats.

A thirteenth non-limiting example takes the form of a system as in any of the first to twelfth non-limiting examples, wherein the implantable medical device system comprises a canister housing operational circuitry including at least the self-correlation means and analysis means, and a lead system including at least some of the plurality of electrodes. FIGS. 1-2 illustrate canisters and lead systems.

A fourteenth non-limiting example takes the form of a system as in the thirteenth non-limiting example, wherein the canister and lead system are configured for implantation as a subcutaneous-only system. A subcutaneous-only system is shown in FIG. 1.

A fifteenth non-limiting example takes the form of a system as in the thirteenth non-limiting example, wherein the canister and lead system are configured for implantation as a transvenous system. A transvenous system is shown in FIG. 2.

A sixteenth non-limiting example takes the form of a method of iterative analysis of cardiac signals comprising: sensing cardiac signals from a plurality of electrodes; generating a self-correlation function from the sensed cardiac signals, the self-correlation function having amplitudes as a function of lag depth; and determining a first estimate of cardiac rate using the self-correlation function; wherein the step of generating the self-correlation function includes: selecting a first data set from the cardiac signal having a first length, N, and a second data set from the cardiac signal having a second length approximately twice the length of the first length, wherein the second data set includes the first data set; repeatedly subtracting the first data set from the second data set at a series of lag depths from approximately zero to approximately N, to generate the self-correlation function.

A seventeenth non-limiting example takes the form of a method as in the sixteenth non-limiting example further comprising identifying amplitude peaks in the self-correlation function and finding a first estimate of cardiac rate. A eighteenth non-limiting example takes the form of a method as in the sixteenth or seventeenth non-limiting examples wherein the step of generating the self-correlation function includes normalizing results of the repeated subtracting step.

A nineteenth non-limiting example takes the form of a method as in any of the sixteenth to eighteenth non-limiting examples wherein the step of determining a first estimate of cardiac rate includes identifying a peak in the self-correlation having a first lag depth, wherein the peak is analytically determined to be likely to indicate reliably high correlation of the first data set to the second data set at the first lag depth, and calculating the cardiac rate using the first lag depth.

A twentieth non-limiting example takes the form of a method comprising repeatedly performing a method as in any one of the sixteenth to nineteenth non-limiting examples, comparing the first lag depth as identified at the first time to the first lag depth as identified at the second time; and if the comparing step finds similarity of the first lag depths, determining that a reliable rate is likely.

A twenty-first non-limiting example takes the form of a method as in any of the sixteenth to twentieth non-limiting examples, wherein the first data set comprises data from the sensed cardiac signals covering approximately two seconds of data, and the second data set comprises data from the sensed cardiac signals covering approximately four seconds of data.

A twenty-second non-limiting example takes the form of a method as in any of the sixteenth to twentieth non-limiting examples, wherein the first data set comprises data from the sensed cardiac signals covering approximately one second of data, and the second data set comprises data from the sensed cardiac signals covering approximately two seconds of data.

A twenty-third non-limiting example takes the form of a method as in any of the sixteenth to twenty-second non-limiting examples, further comprising determining whether cardiac therapy is needed using at least the first estimate of cardiac rate.

A twenty-fourth non-limiting example takes the form of a method as in any of the sixteenth to twenty-third non-limiting examples, further comprising: detecting R-waves in order to identify a second estimate of cardiac rate therefrom; and selecting from between the first estimate of cardiac rate and the second estimate of cardiac rate to yield a final estimate of cardiac rate.

A twenty-fifth non-limiting example takes the form of an implantable medical device comprising sensing circuitry and a processor and a non-transitory medium with instructions contained therein for implementation by the processor, the processor configured to operate on the instructions to use the sensing circuitry and therapy output circuitry as follows: sensing cardiac signals with the sensing circuitry; generating a self-correlation function from the sensed cardiac signals, the self-correlation function having amplitudes as a function of lag depth, by: selecting a first data set from the cardiac signal having a first length, N, and a second data set from the cardiac signal having a second length approximately twice the length of the first length, wherein the second data set includes the first data set; repeatedly subtracting the first data set from the second data set at a series of lag depths from approximately zero to approximately N, to generate the self-correlation function; and determining a first estimate of cardiac rate using the self-correlation function.

Numerous additional examples take the form of implantable cardiac systems comprising a canister housing operational circuitry, the operational circuitry being configured for use with a plurality of electrodes, wherein operational circuitry is configured to perform the methods of any of the sixteenth to twenty-fourth non-limiting examples.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of iterative analysis of cardiac signals comprising:
sensing cardiac signals from a plurality of electrodes;
generating a self-correlation function from the sensed cardiac signals, the self-correlation function having amplitudes as a function of lag depth; and
determining a first estimate of cardiac rate using the self-correlation function;
wherein the step of generating the self-correlation function includes:
selecting a first data set from the cardiac signal having a first length, N, and a second data set from the cardiac signal having a second length approximately twice the length of the first length, wherein the second data set includes the first data set;
repeatedly subtracting the first data set from the second data set at a series of lag depths from approximately zero to approximately N, to generate the self-correlation function.

2. A method as in claim 1 further comprising identifying amplitude peaks in the self-correlation function and finding a first estimate of cardiac rate.

3. A method as in claim 2 wherein the step of generating the self-correlation function includes normalizing results of the repeated subtracting step.

4. A method as in claim 3 wherein the step of determining a first estimate of cardiac rate includes identifying a peak in the self-correlation having a first lag depth, wherein the peak is analytically determined to be likely to indicate reliably high correlation of the first data set to the second data set at the first lag depth, and calculating the cardiac rate using the first lag depth.

5. A method comprising:
performing the method of claim 4 at a first time;
repeating the method of claim 4 at a second time;
comparing the first lag depth as identified at the first time to the first lag depth as identified at the second time; and
if the comparing step finds similarity of the first lag depths, determining that a reliable rate is likely.

6. A method as in claim 1 wherein the first data set comprises data from the sensed cardiac signals covering approximately two seconds of data, and the second data set comprises data from the sensed cardiac signals covering approximately four seconds of data.

7. A method as in claim 1 wherein the first data set comprises data from the sensed cardiac signals covering approximately one second of data, and the second data set comprises data from the sensed cardiac signals covering approximately two seconds of data.

8. A method as in claim 1 further comprising determining whether cardiac therapy is needed using at least the first estimate of cardiac rate and, if so, delivering cardiac therapy.

9. A method as in claim 1 further comprising:
  detecting R-waves in order to identify a second estimate of cardiac rate therefrom; and
  selecting from between the first estimate of cardiac rate and the second estimate of cardiac rate to yield a final estimate of cardiac rate.

10. An implantable cardiac system comprising a canister housing operational circuitry, the operational circuitry being configured for use with a plurality of electrodes, the operational circuitry being configured to operate as follows:
  sensing cardiac signals by receiving electrical signals from the plurality of electrodes;
  generating a self-correlation function from the sensed cardiac signals, the self-correlation function having amplitudes as a function of lag depth, by:
    selecting a first data set from the cardiac signal having a first length, N, and a second data set from the cardiac signal having a second length approximately twice the length of the first length, wherein the second data set includes the first data set;
    repeatedly subtracting the first data set from the second data set at a series of lag depths from approximately zero to approximately N, to generate the self-correlation function; and
  determining a first estimate of cardiac rate using the self-correlation function.

11. A system as in claim 10 wherein the operational circuitry is configured such that determining a first estimate of cardiac rate using the self-correlation function includes identifying amplitude peaks in the self-correlation function and finding a first estimate of cardiac rate.

12. A system as in claim 11 wherein the operational circuitry is configured such that generating the self-correlation function includes normalizing results of the repeated subtracting step.

13. A system as in claim 12 wherein the operational circuitry is configured such that determining a first estimate of cardiac rate includes identifying a peak in the self-correlation having a first lag depth, wherein the peak is analytically determined to be likely to indicate reliably high correlation of the first data set to the second data set at the first lag depth, and calculating the cardiac rate using the first lag depth.

14. A system as in claim 13 wherein the operational circuitry is configured to generate at least first and second estimates of cardiac rate at first and second times using first and second lag depths, to compare the first lag depth and the second lag depth and determine that a reliable cardiac rate calculation has occurred if the first and second lag depths are similar.

15. A system as in claim 10 wherein the operational circuitry is configured such that the first data set comprises data from the sensed cardiac signals covering approximately two seconds of data, and the second data set comprises data from the sensed cardiac signals covering approximately four seconds of data.

16. A system as in claim 10 wherein the operational circuitry is configured such that the first data set comprises data from the sensed cardiac signals covering approximately one second of data, and the second data set comprises data from the sensed cardiac signals covering approximately two seconds of data.

17. A system as in claim 10 wherein the operational circuitry comprises therapy delivery circuitry for generating an electrical stimulus output, and the operational circuitry is further configured to determine whether cardiac therapy is needed using at least the first estimate of cardiac rate and, if so, to deliver cardiac therapy using the therapy delivery circuitry.

18. A system as in claim 10 wherein the operational circuitry is configured to:
  detect R-waves in the sensed cardiac signals to calculate a second estimate of cardiac rate therefrom; and
  select from between the first estimate of cardiac rate and the second estimate of cardiac rate to yield a final estimate of cardiac rate.

19. A system as in claim 18 wherein the operational circuitry comprises therapy delivery circuitry for generating an electrical stimulus output, and the operational circuitry is further configured to determine whether cardiac therapy is needed using at least the first estimate of cardiac rate and, if so, to deliver cardiac therapy using the therapy delivery circuitry.

20. An implantable medical device comprising sensing circuitry and a processor and a non-transitory medium with instructions contained therein for implementation by the processor, the processor configured to operate on the instructions to use the sensing circuitry and therapy output circuitry as follows:
  sensing cardiac signals with the sensing circuitry;
  generating a self-correlation function from the sensed cardiac signals, the self-correlation function having amplitudes as a function of lag depth, by:
    selecting a first data set from the cardiac signal having a first length, N, and a second data set from the cardiac signal having a second length approximately twice the length of the first length, wherein the second data set includes the first data set;
    repeatedly subtracting the first data set from the second data set at a series of lag depths from approximately zero to approximately N, to generate the self-correlation function; and
  determining a first estimate of cardiac rate using the self-correlation function.

* * * * *